US009546936B2

(12) United States Patent
Rowlen et al.

(10) Patent No.: US 9,546,936 B2
(45) Date of Patent: Jan. 17, 2017

(54) PROCESSING BIOLOGICAL MATERIAL FOR FLOW CYTOMETRY EVALUATION FOR VIRUS PARTICLES

(71) Applicant: VIROCYT, INC., Boulder, CO (US)

(72) Inventors: Kathy L. Rowlen, Boulder, CO (US); Erica Dawson Tenent, Broomfield, CO (US); Lauren R. Wolfe, Boulder, CO (US)

(73) Assignee: VIROCYT, INC., Arvada, CO (US)

( * ) Notice: Subject to any disclaimer, the term of this patent is extended or adjusted under 35 U.S.C. 154(b) by 0 days.

(21) Appl. No.: 14/947,708

(22) Filed: Nov. 20, 2015

(65) Prior Publication Data
US 2016/0076981 A1 Mar. 17, 2016

Related U.S. Application Data

(62) Division of application No. 14/422,446, filed as application No. PCT/US2014/044423 on Jun. 26, 2014.

(60) Provisional application No. 61/840,688, filed on Jun. 28, 2013.

(51) Int. Cl.
| | |
|---|---|
| C12N 7/02 | (2006.01) |
| G01N 1/34 | (2006.01) |
| B01D 15/38 | (2006.01) |
| B01J 20/28 | (2006.01) |
| C12N 7/00 | (2006.01) |
| B01D 15/32 | (2006.01) |
| B01D 15/34 | (2006.01) |
| G01N 1/40 | (2006.01) |
| G01N 15/14 | (2006.01) |
| G01N 15/10 | (2006.01) |

(52) U.S. Cl.
CPC .............. *G01N 1/34* (2013.01); *B01D 15/327* (2013.01); *B01D 15/34* (2013.01); *B01D 15/3847* (2013.01); *B01J 20/28092* (2013.01); *C12N 7/00* (2013.01); *G01N 15/14* (2013.01); *C12N 2760/16051* (2013.01); *G01N 1/4077* (2013.01); *G01N 15/1459* (2013.01); *G01N 2015/1006* (2013.01)

(58) Field of Classification Search
None
See application file for complete search history.

(56) References Cited

U.S. PATENT DOCUMENTS

| | | | |
|---|---|---|---|
| 6,843,996 B1* | 1/2005 | Parkin ................. | C07K 14/005 424/206.1 |
| 2005/0186223 A1* | 8/2005 | Williams ............. | A61K 39/145 424/209.1 |
| 2006/0051583 A1* | 3/2006 | Lau ...................... | B01J 20/3293 428/407 |
| 2010/0105074 A1* | 4/2010 | Covey ............... | G01N 35/00722 435/7.1 |

FOREIGN PATENT DOCUMENTS

WO 2010132053 A1 11/2010

OTHER PUBLICATIONS

Vivaclear Centrifugal Filters, Sartorious Stedim biotech, product description from website last modified Mar. 3, 2008, https://www.sartorius.com/fileadmin/fm-dam/sartorius_media/Lab-Products-and-Services/Lab-Filtration/Ultrafiltration-Devices/Vivaspin-Centrisart/Data-Sheets/Data_Vivaclear-Centrifugal-Filters_SLU2010-e.pdf.*
Ferris Matthew M. et al. "Evaluation of the Virus Counter® for rapid baculovirus quantitation," Journal of Virological Methods, Elsevier B.V., 2011, pp. 111-116.
Loret, S. et al. "Analysis of Herpes Simplex Virus Type I Nuclear Particles by Flow Cytometry," Cytometry Part A, vol. 81A, 2012, pp. 950-959.
Stepp, P.C. et al. "Comparing H1N1 Virus Quantification with a Unique Flow Cytometer and Quantitative PCR," Bioprocess International, vol. 9(8)s, 2011, pp. 50-56.
"Purification of influenza A/H1N1 using CaptoTM Core 700", Application note 29-0003-34 AA, GE Healthcare Bio-Sciences AB, Uppsala, Sweden, 2012, 8 pages.
Glaser, Vicki. "Separation of Therapeutic Biomolecules. Mixed-Mode Chromatography, Layered Bead Designs, In Silico Modeling Used at Large Scale," Genetic Engineering & Biotechnology News, vol. 33, No. 9, 2013, www.genengnews.com, 6 pages.
Kon, Theone et al. "Chromatography for the reduction of Ovalbumin during pilot-scale Influenza virus purification from eggs," BioProcess International, Apr. 17-18, 2013, Dusseldorf, Germany. Institute for Translational Vaccinology, Bilthoven, The Netherlands, www.intravacc.com, 1 page.

(Continued)

*Primary Examiner* — Stacy B Chen
(74) *Attorney, Agent, or Firm* — Marsh Fischmann & Breyfogle LLP; Ross E. Breyfogle

(57) ABSTRACT

In a method for processing biological materials for flow cytometry evaluation for virus particles, a mixture including biological material and purification particles is centrifuged to prepare a centrifuged composition including a supernatant that may be further processed prior to the flow cytometry evaluation. The purification particles include porous cores functionalized to capture smaller-size impurities in a biological material sample and a porous size-exclusion shell surrounding the core to exclude larger-size components of the biological material from entering into the core. Multiple samples may be processed in multi-sample processing units. A product may contain a sealed container with the unit (Continued)

quantity of purification particle in a storage liquid and a kit may include such a sealed container and a centrifugal filter.

19 Claims, 22 Drawing Sheets

(56) References Cited

OTHER PUBLICATIONS

Lundgren, Mats. "Building the Vaccine Manufacturing Platforms of the Future: Disposable Manufacturing," GE Healthcare Bio-Sciences AB, Uppsala, Sweden, 2012, 23 pages.
Masters, Andy. Types of Ion Exchange Chromatography Media, GE Healthcare Bio-Sciences AB, Uppsala, Sweden, 2011, 28 pages.
"Capto Core 700", Data file 28-9983-07 AA, GE Healthcare Bio-Sciences AB, Uppsala, Sweden, 2012, 4 pages.

* cited by examiner

PROCESSING BIOLOGICAL MATERIAL FOR FLOW CYTOMETRY EVALUATION FOR VIRUS PARTICLES

REFERENCE TO RELATED APPLICATIONS

This application is a divisional of U.S. patent application Ser. No. 14/422,446 entitled "PROCESSING BIOLOGICAL MATERIAL FOR FLOW CYTOMETRY EVALUATION FOR VIRUS PARTICLES", which is a U.S. national stage under the Patent Cooperation Treaty of international patent application no. PCT/US2014/044423 filed Jun. 26, 2014, which claims a benefit to U.S. provisional patent application No. 61/840,688 entitled "PROCESSING BIOLOGICAL MATERIAL FOR FLOW CYTOMETRY EVALUATION FOR VIRUS PARTICLES" filed Jun. 28, 2014, and the entire contents of each of the aforementioned applications are incorporated herein by reference.

FIELD OF THE INVENTION

The disclosure relates to flow cytometry evaluation of biological materials in relation to the presence of virus particles and preparation of biological materials in anticipation of flow cytometry evaluation.

BACKGROUND OF THE INVENTION

Flow cytometry is an analytical technique used in a number of applications to measure physical and/or chemical properties of biological or non-biological particles as they flow in a sample fluid through an investigation cell. Flow through the cell may be investigated by a variety of techniques, including subjecting the flow to electrical, acoustic and/or optical signals and measuring and analyzing responses to detect and evaluate particles in the sample.

Flow cytometers have found wide use in analyzing biological particles having a size on the order of bacteria or cells, typically in a range of 1 to 15 microns in size. However, accurate flow cytometry evaluation of virus particles presents particular problems because of the very small size of virus particles, which typically have a size on the order of tens to hundreds of nanometers.

One approach that has been proposed for flow cytometry evaluation for virus particles is the use of flow cytometers operated at extremely low sample flow rates on the order of 5000 nanoliters per minute or smaller and with continuous monitoring and control of sample flow rate. This approach has been effective to a significant extent, but it is still difficult to accurately and quickly evaluate the extremely small virus particles relative to other biological material components and to accurately control the flow of samples containing a mixture of different biological material components.

SUMMARY OF THE INVENTION

Flow control and evaluation accuracy may be improved in relation to flow cytometry evaluation for virus through preparatory processing of biological material samples to be evaluated prior to flow cytometry evaluation. This may be particularly beneficial when using flow cytometers that are designed to operate at very low sample fluid flow rates. Removing components of the biological material sample that are larger than virus particles may reduce potential for flow obstruction or plugging that might otherwise occur during flow cytometry. Removing impurities smaller than virus particles may improve detection accuracy for virus particles.

A first aspect of this disclosure involves a method for processing biological material, such as in anticipation of possible flow cytometry evaluation for virus particles. The method includes centrifuging a mixture comprising biological material for evaluation and purification particles to prepare a centrifuged composition including a more-dense phase concentrated in the purification particles and a less-dense supernatant. The biological material includes larger-size components and smaller-size components. The purification particles comprise a porous core, which is functionalized to capture at least some impurities of the smaller-size components, and a porous size-exclusion shell. The shell surrounds the core and has a pore structure to exclude the larger-size components from entering into the core through the pore structure of the shell while permitting the smaller-size components to enter into the core through the pore structure of the shell.

A number of feature refinements and additional features are applicable to this first aspect. These feature refinements and additional features may be used individually or in any combination within the subject matter of the first aspect or any other aspect of the disclosure. As such, each of the following features may but are not required to be, used with any other feature or a combination of features of the first aspect or any other aspect.

The biological material may be from any source. One beneficial application is in relation to processing biological material in allantoic fluid samples containing influenza virus obtained from chicken eggs, for example as may be produced in relation to investigation or manufacture of influenza vaccines. As will be appreciated, one technique for manufacturing influenza vaccine involves inoculation of fertilized chicken eggs with influenza virus and growing viruses within the eggs. Viruses may be harvested from the allantoic fluid in the eggs and used to prepare influenza vaccines.

The method may include processing each feed sample of biological material separately in preparation for flowing cytometry evaluation. Alternatively, the method may include processing a plurality of feed samples of biological methods in preparation for flow cytometry evaluations. Processing a plurality of samples may include the use of multi-sample processing units.

In addition to virus particles that may be the subject of a desired flow cytometry evaluation, a biological material sample may include other biological components that may complicate or interfere with effective operation of flow cytometry equipment and/or effective detection, differentiation or quantification of virus particles within the biological material sample. The larger-size components may include particles of a virus size (e.g., virus particles). The larger-size components of the biological material may include components that are larger than virus particles of interest for evaluation. The smaller-size components of the biological material may include components that are smaller than virus particles of interest for evaluation. In the case of biological material samples including influenza virus, such as allantoic fluid obtained from eggs, larger-size components may for example include, in addition to possible virus particles, one or more components such as cell debris, chicken embryo debris, bacteria, protein aggregates, lipids, lipid assemblies, lipid-protein assemblies, lecithins, lipid-protein aggregates, liposomes, ribosomes, vesicles, protein-nucleic acid complexes or other materials. Such larger-size components may significantly interfere with effective operation of flow cytometry equipment for accurate evaluation for virus particles. A variety of impurities may be present in smaller-size components of a biological material sample that may both complicate effective operation of flow cytometry equipment and may complicate differentiation, counting and/or quantification of virus particles. Examples of some possible impurities in such smaller-size components may include proteins and/or nucleic acids, and may include material derived from viruses, such as fragments or debris from viruses. In many situations when performing flow cytometry evaluation for virus particles, it is an objective to identify, count and quantify only in-tact virus particles, and not virus-related debris or fragments.

The method may include flow cytometry evaluation of a sample including at least a portion of the supernatant produced by the centrifuging, with or without additional intermediate processing of the supernatant or portions thereof between the centrifuging and the flow cytometry. Such additional intermediate processing may include, for example, one or more of the following operations: addition of reagents, further purification of biological material in the supernatant, filtration of supernatant, adjusting solute levels, adjusting pH or other processing to prepare a sample in a form or with properties for possible flow cytometry evaluation of biological material in the sample for virus particles.

The method may include, after the centrifuging, filtering a liquid-containing composition comprising at least a portion of the supernatant. Such supernatant may comprise at least a portion of the larger-size components, and may also comprise at least a portion of the smaller-size components not captured by the purification particles. The filtering may include filtering out as a retentate at least a portion, or at least a majority by mass or even substantially all, of the larger-size components that are larger than virus size from the liquid-containing composition. The filtering may include filtration at a separation size to pass at least a portion, or at least a majority by mass or even substantially all, particles of a virus size in filtrate, such that a filtrate from such a filtering step may include at least a portion, at least a majority by mass or even substantially all, virus particles from the liquid-containing composition that would be the subject of flow cytometry evaluation. The filtrate may be concentrated in smaller-size components that are smaller than a virus size relative to the liquid-containing composition subjected to the filtering. The method may include flow cytometry evaluation of a sample comprising at least a portion of the filtrate for the presence of virus particles. The filtering may include centrifugal filtration, for example wherein the liquid-containing composition is centrifuged in a receptacle including a filter element through which filtrate passes for collection during the centrifuging. Retentate is retained on the upstream side of such filter element. The filtering may be performed at a separation size for making a desired filtration separation between at least a portion of the larger-size components of the biological material that are larger than a virus size and particles of a virus size or smaller. The separation size may be selected so that in-tact, unaggregated virus particles will pass through the filter for collection with filtrate. The separation size may often be smaller than about 2 microns, smaller than about 1.5 microns, smaller than about 1.3 microns, or even smaller than about 1 micron. In some embodiments the separation size may be not larger than 2 microns, not larger than 1.5 microns, not larger than 1.3 microns, not larger than 1 micron, not larger than 0.9 micron, not larger than 0.8 micron or not larger than 0.75 micron. The separation size may often be at least 0.05 micron, at least 0.1 micron, at least 0.3 micron, at least 0.4 micron, at least 0.5 micron, at least 0.6 micron or at least 0.7 micron. The volume of filtrate collected during the filtering may be any convenient volume for a single sample of biological material to be processed for flow cytometry evaluation. The filtrate may in some embodiments have a volume of at least 50 microliters, at least 75 microliters, at least 100 microliters, at least 200 microliters, at least 300 microliters, at least 400 microliters, or at least 500 microliters. The filtrate may in some embodiments have a volume that is not larger than 100 milliliters, not larger than 50 milliliters, not larger than 10 milliliters, not larger than 1 milliliter, not larger than 700 microliters, not larger than 500 microliters, or not larger than 300 microliters. For some preferred embodiments, the filtrate may have a volume in a range of from 300 microliters to 700 microliters, such as when processing a single sample of biological material. For some other preferred embodiments, the filtrate may have a volume on a range of from 150 microliters to 400 microliters, such as when simultaneously processing a plurality of samples of biological material.

When the method includes flow cytometry evaluation, the flow cytometry evaluation may be performed using any suitable flow cytometer equipment. In some embodiments, such flow cytometry may include hydrodynamically focusing a flow of the sample to be evaluated and flowing hydrodynamically focused sample through a flow cytometry investigation cell. Hydrodynamic focusing may involve surrounding the sample flow with a flowing sheath fluid prior to introduction into the investigation cell. In some preferred implementations when the method includes flow cytometry evaluation, the flow rate of the sample through the investigation cell may be maintained in a range having a lower limit of 250 nanoliters per minute, 500 nanoliters per minute, 750 nanoliters per minute or 1000 nanoliters per minute and an upper limit of 4000 nanoliters per minute, 3000 nanoliters per minute or 2500 nanoliters per minute. When a plurality of samples are simultaneously processed to prepare the samples for flow cytometry evaluation, the flow cytometry evaluation may advantageously include sequentially feeding the samples to a flow cytometer using an auto sampler.

Preparation of the sample in anticipation of possible flow cytometry evaluation may include marking one or more of the components of the sample with a marker that will aid detection and differentiation of the component. Such a fluorescent maker may also be referred to as a fluorescent stain or fluorescent dye. Such a marker may, for example, be a fluorescent marker with a particular fluorescent emission signature when subjected to incident light. Multiple different markers may be used for different components in the sample that is being prepared for possible flow cytometry evaluation. For example, a first marker in the form of a fluorescent dye having an affinity for nucleic acids (e.g., DNA, RNA) may have a particular fluorescent emission wavelength range and a second marker in the form of a second fluorescent dye with an affinity for one or more proteins may have a different fluorescent emission wavelength range. An in-tact virus particle having both marked protein and marked nucleic acid may have coincidental fluorescent emission events in a flow cytometer investigation cell from both dyes, while fragments including only marked protein or marked nucleic acid would not have coincident fluorescent emission events in the flow cytometer investigation cell. Marking may be performed by contacting biological material or a portion thereof with the marker to attach or otherwise associate with the component or components for which the marker has an affinity. A marker may be contacted with at least a portion of filtrate obtained from a filtration step.

The core of a purification particle may have functionality provided by one or more ligands within the core. The core may include a porous resin matrix to which such ligands are attached. Such ligands may be hydrophobic to attract hydrophobic components from the mixture that enter into the core. Such ligands may have a positive charge to attract components having a negative charge that enter into the core. The size-exclusion shell of the purification particles may have a size-exclusion cutoff, also referred to herein as a molecular weight cutoff, selected to exclude from the core components larger than a particular size. The size exclusion cutoff may be selected to exclude from the core particles of a virus size and larger while permitting smaller-size impurities to move across the shell into the core. In some embodiments, such a size exclusion cutoff may be not larger than 1,500,000 Daltons, not larger than 1,000,000 Daltons, not larger than 900,000 Daltons, not larger than 800,000 Daltons, not larger than 750,000 Daltons or not larger than 700,000 Daltons. In some embodiments, the size-exclusion cutoff may be not smaller than 400,000 Daltons, not smaller than 500,000 Daltons, not smaller than 600,000 Daltons or not smaller than 650,000 Daltons. One particular example of a product that may be used as the purification particles in some embodiments is Capto™ Core 700 (GE Healthcare Life Sciences). Capto™ Core 700 particles include a core having a matrix of highly cross-linked agarose functionalized with ligands that are both hydrophobic and are positively charged and a native agarose base matrix shell. Capto™ Core 700 is reported to have a volume average particle size ($D_{50}$) of 85 microns, octylamine as the functional ligand, and a molecular weight cutoff of about 700,000 Daltons.

The method may include processing to prepare the mixture including biological material and purification particles for use in the centrifuging. Such preparation of the mixture may include any preliminary processing to prepare the mixture in a form and with a composition or properties desired for processing in the centrifuging step. Such preliminary processing may include mixing together ingredients that may include, for example, at least the biological material and the purification particles and may optionally include one or more other ingredients (e.g., buffer solution). The purification particles may be initially provided in a sealed container that contains a unit quantity of the purification particles for use in the mixing step to prepare the mixture with a single biological material sample for flow cytometry evaluation. The preliminary processing may include unsealing the sealed container and removing the purification particles from the unsealed container prior to mixing the purification particles with the biological material. The purification particles as contained in the sealed container may be mixed with storage liquid. Alternatively, biological material may be mixed with the purification particles in the unsealed container.

Preliminary processing of purification particles may include centrifuging the purification particles and such storage liquid to prepare a centrifuged composition with a supernatant of storage liquid above the purification particles. At least a portion of the storage liquid may be removed from the centrifuged composition before the purification particles are mixed with the biological material. The storage liquid may be in the form of a buffer solution, which may be a Tris-HCl buffer solution, and which may include additives such as dissolved salt, surfactant and/or preservative. As will be appreciated, Tris refers to a compound that is also known by the chemical name tris(hydroxymethyl)aminomethane.

One example for such a storage liquid is a Tris-HCl buffer solution, which may optionally include one or more of a dissolved salt (e.g., sodium chloride), a surfactant (e.g., Zwittergent 3-14), a preservative (e.g., sodium azide) or other components. The storage liquid may be suitable for long-term storage of the purification particles to maintain the purification particles in a conditioned state in preparation for use to capture impurities from biological material prior to or during centrifuging a mixture containing the biological material and the purification particles. The storage liquid may have any suitable pH. In some embodiments the storage liquid may have a pH in a range having a lower limit of pH 7, pH 7.5 or pH 7.8 and having an upper limit of pH 9, pH 8.5 or pH 8.2. The storage liquid may be filtered to remove small particles that may be of a size that could provide a false positive for presence of virus, such as by filtration through a 0.02 micron or smaller filter. Because of the small size of the filtration, the filtration may be referred to as sterile filtering. When the storage liquid is a Tris-HCl buffer solution, in some embodiments the storage liquid may include Tris at a concentration of at least 5 millimoles per liter, at least 10 millimoles per liter or at least 12 millimoles per liter. In some embodiments the storage liquid may include Tris at a concentration of not larger than 20 millimoles per liter, not larger than 15 millimoles per liter or not larger than 13 millimoles per liter. When a dissolved salt, such as sodium chloride, is included in the storage liquid, in some embodiments the sodium chloride may be at a concentration of at least 20 millimoles per liter, at least 40 millimoles per liter or at least 45 millimoles per liter. In some embodiments such concentration of dissolved salt may be not larger than 100 millimoles per liter, not larger than 85 millimoles per liter, not larger than 75 millimoles per liter or not larger than 60 millimoles per liter. When the storage liquid contains a surfactant, the surfactant may in some embodiments be present at a concentration, for example, in a range of from 20 to 100 micromoles per liter. When the buffer solution contains a preservative, the preservative may in some embodiments be present for example, at a concentration in a range of from 0.01 weight percent to 0.25 weight percent.

The quantity of purification particles mixed with a biological material in the mixture subjected to the centrifuging may in some embodiments have a bulk volume of at least 25 microliters, at least 35 microliters, at least 50 microliters, at least 100 microliters, at least 150 microliters, at least 200 microliters or at least 350 microliters. In some embodiments, the quantity of the purifications particles in the mixture may have a bulk volume of not more than 70 milliliters, not more than 50 milliliters, not more than 25 milliliters, not more than 10 milliliters, not more than 5 milliliters, not more than 1 milliliter, not more than 500 microliters or not more than 250 microliters. When the purification particles are provided with a storage liquid, a volume ratio of the storage liquid to the bulk volume of the purification particles may in some embodiments be not larger than 10:1, not larger than 5:1, not larger than 4:1, not larger than 3:1, not larger than 2.5:1, or not larger than 2:1. In some embodiments, such a volume ratio of the storage liquid to bulk volume of the purification particles may be at least 0.75:1, at least 0.9:1 at least 1:1 or at least 1.5:1, with a ratio of about from about 1:1 to 2:1 being useful for many situations.

The quantity of biological material mixed with the purification particles in the mixture subjected to the centrifuging may in some embodiments have a volume of at least 30 microliters, at least 45 microliters, at least 60 microliters, at least 125 microliters, at least 150 microliters, at least 200 microliters, at least 250 microliters or at least 450 microliters, In some embodiments, the quantity of the biological material in the mixture may have a volume of not more than 90 milliliters, not more than 65 milliliters, not more than 35 milliliters, not more than 15 milliliters, not more than 7.5 milliliters, not more than 1.5 milliliters, not more than 600 microliters, not more than 400 microliters, not more than 300 microliters, or not more than 250 microliters.

In some embodiments, the mixture may have a total volume of at least 70 microliters, at least 85 microliters, at least 120 microliters, at least 200 microliters, at least 300 microliters, at least 400 microliters, at least 450 microliters or at least 850 microliters. In some embodiments, the mixture may have a total volume of not larger than 170 milliliters, not larger than 125 milliliters, not larger than 70 milliliters, not larger than 25 milliliters, not larger than 15 milliliters, not larger than 2.5 milliliters, not larger than 1.5 milliliters, not larger than 1 milliliter, or not larger than 700 microliters.

When a plurality of samples of biological material are being processed, preparing the mixtures may include processing a plurality of mixtures each including biological material and such a unit quantity of the purification particles, with each mixture prepared in a separate compartment of a multi-sample processing unit. Such sample processing unit may be a sample purification unit having any feature or combination of features as disclosed herein. Mixing biological material with the purification particles may include adding an appropriate quantity of the biological material to each of such multiple containers that may each already have disposed therein a unit quantity of the purification particles.

Preparing the mixture including the purification particles and the biological material may include processing the biological material with any desired preliminary processing to prepare the biological material in a form or with characteristics desired for mixing with the purification particles.

Processing the biological material prior to mixing the biological material with the purification particles may include preliminary centrifuging of a composition including a crude biological material sample. In some embodiments, the crude biological material sample may be diluted with buffer solution (which may also be referred to as buffer solution reagent) prior to the preliminary centrifuging. During the preliminary centrifuging a dense pellet may form with a supernatant above the pellet. The pellet may include, for example, cellular material and particles from the crude biological material sample. After the centrifuging at least a portion of the resulting supernatant may be recovered that includes the biological material in a clarified form to be mixed with the purification particles. The buffer may be a Tris-HCl buffer solution. Such a Tris-HCl buffer solution may include any appropriate concentration of components. In some embodiments, such a Tris-HCl buffer solution may include a concentration of Tris that is 10 millimoles per liter, at least 20 millimoles per liter, at least 50 millimoles per liter, at least 75 millimoles per liter or at least 100 millimoles per liter. In some embodiments, such a Tris-HCl buffer solution may include a concentration of Tris that is not larger than 250 millimoles per liter, 200 millimoles per liter, 150 millimoles per liter, 100 millimoles per liter, 50 millimoles per liter, 30 millimoles per liter, or not larger than 15 millimoles per liter. Such a Tris-HCl buffer solution may include a dissolved salt, such as sodium chloride, which may in some embodiments be at a concentration of at least 40 millimoles per liter, at least 75 millimoles per liter, at least 100 millimoles per liter, at least 200 millimoles per liter, at least 300 millimoles per liter or least 400 millimoles per liter. In some embodiments, such a dissolved salt concentration may be not larger than 1 mole per liter, not larger than 800 millimoles per liter or not larger than 600 millimoles per liter, not larger than 400 millimoles per liter, not more than 300 millimoles per liter or not more than 200 millimoles per liter. The Tris-HCl buffer solution may also include a surfactant (e.g., Zwittergent 3-14) and/or or a preservative (e.g., sodium azide) at any convenient concentration. In some embodiments, such a Tris-HCl buffer solution may include a surfactant at a concentration, for example, in a range of from 200 to 1000 micromoles per liter. In some embodiments, such a Tris-HCl buffer solution may include a preservative at a concentration in a range of from having an lower limit of 0.01 weight percent or 0.1 weight percent and an upper limit of 2.5 weight percent or 0.25 weight percent. Such a Tris-HCl buffer solution may in some embodiments be filtered to remove small particles that may have a size that could provide a false positive for presence of virus, such for example filtration through a 0.02 micron or smaller filter. In some embodiments, such a Tris-HCl buffer solution may have a pH in a range having a lower limit of pH 7 or pH 7.5 or 7.8 in an upper limit of pH 9, pH 8.5 or pH 8.2. When a plurality of samples of biological material are being processed, such preliminary centrifuging may include centrifuging a multi-sample processing unit comprising a plurality of crude biological material samples diluted with buffer solution. Such multi-sample processing unit may be a sample clarification unity having any feature or combination of features as disclosed herein. A crude biological material sample may be added to each of such multiple contains that already have been disposed therein an appropriate quantity of the buffer solution.

Prior to being centrifuged, the mixture including the biological material and the purification particles may be intimately contacted for some period of time to promote effective capture of smaller-size impurities within the cores of the purification particles. Intimate contact between the biological material and the purification particles may be promoted by mixing or agitating the mixture of some period of time; for example, by agitating contents of a container for some time by hand and/or on a mechanical shaker. The mixture may contain relative proportions of purification particles, biological material and/or other optional components to maintain the purification particles in a slurried form to promote good contact for capturing impurities and to permit easy manipulation of the mixture. In some embodiments, the mixture may include a ratio of the bulk volume of purification particles to the volume of the biological material of at least 0.4:1, at least 0.5:1, at least 0.6:1, at least 0.7:1, at least 0.75:1, or at least 1:1. In some embodiments, such a ratio may be not larger than 2:1, not larger than 1.5:1, not larger than 1:1, not larger than 0.9:1 or not larger than 0.8:1. The mixture may optionally include buffer solution (e.g., Tris-HCl buffer solution), which may be as noted above in relation to processing the biological material prior to mixing with the purification particles. The buffer solution may help to adjust properties of the mixture, such as pH or salinity, to promote effective capture of impurities in the cores of the purification particles and may also provide additional liquid to assist in slurrying the purification particles. In some embodiments, the mixture may include a ratio of the volume of such buffer solution to the volume of the biological material of at least 1:20, at least 1:15, at least 1:10, at least 1:9, at least 1:5, at least 1:2, or at least 1:1. In some embodiments, such a ratio may be not larger than 2:1, not larger than 1:1, not larger than 1:2, not larger than 1:5, or not larger than 1:8. In some embodiments, the mixture may include a ratio of the bulk volume of the purification particles to total volume of liquid (e.g., total biological material plus buffer solution) of at least 0.3:1, at least 0.4:1, at least 0.5:1, at least 0.6:1 or at least 0.65:1. In some embodiments, such a ratio may be not larger than 0.9:1 or not larger than 0.8:1 or not larger than 0.75:1.

When a plurality of samples are being processed, centrifuging a mixture with biological material and purification particles may include simultaneously centrifuging a plurality of such mixtures with each such mixture disposed in a different fluid container of a multi-sample processing unit, which may be a sample purification unit having any feature or features as disclosed herein. Such a multi-sample processing unit may be centrifuged with such plurality of mixture disposed in such fluid containers.

When a plurality of samples are being processed, filtering a liquid-containing composition may include simultaneously filtering a plurality of such liquid-containing composition, which may each include at least a portion of a different such surfactant from centrifuging a plurality of mixtures with biological material and purification particles. The filtering may therefore prepare a plurality of retentates with purification particles and a plurality of filtrates. The filtering may be performed with a plurality of mixtures with biological materials and purification particles initially received in different filter wells of a multi-well sample filtration unit, such as a sample filtration unit being or having any combination of features disclosed herein. Such sample filtration unit may include a plurality of filtrate collection containers, each of which may collect a different filtrate from filtration of a different mixture. The filtering may include centrifugal filtering, for example, simultaneously centrifugal filtration of a plurality of samples by centrifuging such a sample filtration unit.

A second aspect of this disclosure involves a product useful in the preparation of samples of biological material for possible flow cytometry evaluation for virus particles. The biological material may comprise larger-size components including virus particles and smaller-size components including non-virus impurities. The product includes a sealed container containing a mixture sealed within the container. The mixture includes a unit quantity of purification particles for processing a single sample of the biological material for flow cytometry evaluation for virus particles. The purification particles include a porous core functionalized to capture at least some impurities that may be in the smaller-size components of the biological material. The purification particles also include a porous, size-exclusion shell surrounding the core and having a pore structure to exclude the larger-size components from entering into the core through the pore structure of the shell while permitting the smaller-size components to enter into the core through the pore structure of the shell. The mixture also includes a Tris-HCl buffer solution storage liquid.

A number of feature refinements and additional features are applicable to this second aspect. These feature refinements and additional features may be used individually or in any combination within the subject matter of the second aspect or any other aspect of the disclosure. As such, each of the following features may, but are not required to be, used with any other feature or combination of features of the second aspect or any other aspect.

The sealed container and/or the mixture within the sealed container may be or have features as described with respect to the first aspect or a third aspect of this disclosure, discussed below. The biological material for which the product may be designed may be or include features of the biological material or crude biological material samples as described with respect to the first aspect. The sealed container may be one of a plurality of sealed containers of a sample purification unit, for example a sample purification unit described with respect to a fourth aspect of this disclosure, discussed below. Each one of such a plurality of sealed containers may contain a unit quantity of purification particles for processing a single sample of biological material, so that the sample purification unit may be used to process a plurality of samples of biological material for flow cytometry evaluation.

A third aspect of this disclosure involves a kit that may be useful to prepare samples of biological material for possible flow cytometry evaluation for virus particles. The kit includes at least one sealed container containing a unit quantity of purification particles for processing a single sample of the biological material for flow cytometry evaluation for virus particles. The purification particles include a porous core functionalized to capture at least some biological impurities that may be in smaller-size components of the biological material. The purification particles also include a porous, size-exclusion shell surrounding the core and having a pore structure to exclude the larger-size components of the biological material from entering into the core through the pore structure of the shell while permitting the smaller-size components to enter into the core through the pore structure of the shell. The kit also includes at least one centrifugal filter for centrifugal filtration of at least a portion of the biological material after treatment with the purification particles, to prepare filtrate for flow cytometry evaluation for virus particles.

A number of feature refinements and additional features are applicable to this third aspect. These feature refinements and additional features may be used individually or in any combination within the subject matter of the third aspect or any other aspect of the disclosure. As such, each of the following features may, but are not required to be, used with any other feature or combination of features of the third aspect or any other aspect.

The sealed container, purification particles and centrifugal filter may be or include features as described with respect to the first aspect or the second aspect. The sealed container may include a mixture including purification particles and buffer solution storage liquid, or features thereof, described with respect to the first aspect or the second aspect. The sealed container and the purification particles may be present in the kit in the form of the product of the second aspect. The components of the kit may be enclosed in common packaging, for example enclosed in a common bag, wrapping, box or packaging container. The biological material for which the kit may be designed may be or include features of the biological material or crude biological material samples as described with respect to the first aspect or the second aspect. The kit of the third aspect may be a kit according to the fourth aspect, discussed below. The kit of the third aspect may include any one or more of, or all of, a sample clarification unit, sample purification unit or sample filtration unit, which may be or include a feature or features as disclosed in relation to the fourth aspect. The centrifugal filter of the third aspect may be provided in such a sample filtration unit, which may include a plurality of centrifugal filters in the form of multiple combinations of a filter well and corresponding filtrate collection container.

A fourth aspect of this disclosure involves a kit that may be useful to prepare samples of biological material for flow cytometry evaluation for virus particles for example according to processing as disclosed herein. The kit includes a plurality of multi-sample processing units, with the multi-sample processing units including at least a sample purification unit. Such sample purification unit includes a plurality of fluid containers each having disposed therein of volume of a mixture which may be useful for purifying samples of biological materials prior to flow cytometry evaluation for virus particles. The mixture within each fluid container may comprise a unit quantity of purification particles and a buffer solution storage liquid.

A number of feature refinements and additional features are applicable to this third aspect. These feature refinements and additional features may be used individually or in any combination within the subject matter of the fourth aspect or any other aspect of the disclosures. As such, each of the following features may, but are not required to be, used within any other feature or combination of features of the fourth aspect or any other aspect.

The purification particles may be as described with respect to any of the first, second and third aspects. Such purification particles may, for example, include a porous core functionalized to capture at least some non-virus impurities and a porous size-exclusion shell surrounding the core and having a pore structure to exclude larger-size components from entering into the core through the pore structure of the shell and to permit the smaller-size components to enter into the core through the pore structure of the shell. The buffer solution storage liquid may have one or more properties as described for storage liquid in relation to any of the first, second and third aspects.

The sample purification unit may include the plurality of fluid containers in any convenient form. The sample purification unit may include a plurality of fluid containers in the form of tubes, which may be received in a tube rack, or holder. As an alternative, the sample purification unit may include a multi-well plate and the fluid containers of the sample purification unit may be in the form of the wells in the plate. When the fluid containers comprise tubes, the tubes may be provided in a plurality of tube strips, with each tube strip comprising multiple ones of the tubes connected together. Any convenient number of tubes may be included in each tube strip. Such tube strips may each have the same number of tubes. The fluid containers of the sample purification unit may be sealed with the mixture of purification particles and storage liquid disposed therein. In the case of tubes, each tube may be sealed with a cap. Such caps may be provided in the form of cap strips each containing a number of caps that corresponds with a single strip of tubes. When fluid containers are provided in the form of wells in a multi-well plate, the wells may be capped with a single cap that seals all of the fluid-containment wells at the top of the multi-well plate. The sample purification unit may include a cover that mates with a rack or multi-well plate to cover the tops of the fluid containers and which may protection enhanced protection during storage, transportation and handling.

The fluid containers of the sample purification unit may each have a total fluid containment volume of a convenient size for the sample being processed. The fluid containers of the sample purification unit often may each have a total fluid containment volume of at least 50 microliters, at least 100 microliters, at least 500 microliters or at least 1 milliliter. The fluid containers of the sample purification unit often may each have a total fluid containment volume of up to 50 milliliters, up to 15 milliliters, up to 10 milliliters, up to 5 milliliters, up to 2 milliliters or up to 1.5 milliliters. The fluid purification unit may include any convenient number of the fluid containers. The sample purification may include at least 6, at least 12, at least 24, at least 48, at least 72 or at least 96 of the fluid containers. The sample purification plate may include up to 384, up to 192, up to 128 or up 96 of the fluid containers. The mixture disposed in each of the fluid containers may include a ratio of volume of the buffer solution storage liquid to bulk volume of the purification particles as described with respect to any of the first, second and third aspects. Each second fluid container may have a total containment volume of at least two times, at least three times or at least four times as large as the bulk volume of purification particles in the mixture contained in the fluid container. Such a total containment volume of each fluid container may be not larger than 10 times, not larger than 8 times, not larger than 6 times or not larger than 4 times as large as the bulk volume of the purification particles in the fluid container. Providing extra volume in the fluid container over the bulk volume of the purification particles in the fluid container may be conveniently provide available volume to receive clarified sample of biological material to permit such clarified sample material to be mixed with the purification particles for further processing, for example for further sample purification prior to flow cytometry evaluation for virus particles.

The multi-sample processing units of the fourth aspect may include a sample clarification unit including a plurality of fluid containers each having a fluid containment volume with a first portion of the fluid containment volume occupied by a volume of buffer solution reagent and a second portion of the fluid containment volume available to receive a sample of biological material to mix with such a volume of buffer solution reagent in such a fluid container of the sample clarification unit. Each of the fluid containers of the sample clarification unit may be sealed with the volume of buffer solution reagent disposed therein. The fluid containers of the sample clarification unit may be in the form of tubes received in a tube rack, or holder. Such tubes may be in the form of a plurality of tube strips, with each tube strip comprising multiple ones of the tubes connected together. Each such tube may be sealed with a cap. When the tubes are provided in tube strips, such caps may be provided in corresponding tube strips with a number of caps corresponding with a number of tubes in each tube strip. Such fluid containers of the sample clarification unit may each have a total fluid containment volume of a convenient size for the sample being processed. The fluid containers of the sample clarification unit may each have a total fluid containment volume that is the same as, larger than, or smaller than the total fluid containment volume of each of the fluid containers of the sample purification unit. The fluid containers of the sample clarification unit often may each have a total fluid containment volume of at least 50 microliters, at least 100 microliters, at least 500 microliters or at least 1 milliliter. The fluid containers of the sample clarification unit often may each have a total fluid containment volume of up to 50 milliliters, up to 15 milliliters, up to 10 milliliters, up to 5 milliliters, up to 2 milliliters or up to 1.5 milliliters. The volume of buffer solution reagent in each of the containers of the sample clarification unit may be in a range having a lower limit of 30 microliters, 45 microliters, 60 microliters, 125 microliters, 250 microliters or 450 microliters and an upper limit of 35 milliliters, 15 milliliters, 10 milliliters, 7.5 milliliters, 1.5 milliliters, 600 microliters or 250 microliters, provided that the upper limit is larger than the lower limit. The buffer solution reagent may be as described with respect to any of the first, second or third aspects. A preferred buffer solution reagent is a Tris-HCl buffer solution, preferably having a pH in a range of from pH to pH 9. In some preferred implementations, such a Tris-HCl buffer solution used for the buffer solution reagent may include Tris at a concentration of at least 10 millimoles per liter, at least 20 millimoles per liter or at least 25 millimoles per liter. Such buffer solution reagent may include a Tris at a concentration of not larger than 40 millimoles per liter or not larger than 30 millimoles per liter. When dissolved salts such as sodium chloride is included in the buffer solution reagent, the sodium chloride in some preferred implementations may be at a concentration of at least 40 millimoles per liter, at least 80 millimoles per liter or at least 90 millimoles per liter. In some preferred implementations, such concentration of dissolved salt may be not larger than 200 millimoles per liter, not larger than 170 millimoles per liter, not larger than 150 millimoles or not larger than 120 millimoles per liter. Such buffer solution reagent may include a concentration of Tris that is at least as large as, at least two times as large as or at least four times as large as a concentration of Tris in the buffer solution storage liquid of the sample purification unit. Such a buffer solution reagent may include a concentration of sodium chloride that is at least as large as, at least two times as large as or at least four times as large as a concentration of sodium chloride in the buffer solution storage liquid of the sample purification unit. The unit quantity of the purification particles in each of the fluid containers of the sample purification unit may have a bulk volume that is larger than a volume of the buffer solution reagent in each of the fluid containers of the sample clarification unit. The sample clarification unit may include any convenient number of fluid containers. The number of fluid containers in the sample clarification unit may be as described for the sample purification unit and may conveniently be equal to the number of fluid containers in the sample purification unit to facilitate convenient processing of such a number of samples of biological material through different processing stages prior to flow cytometry evaluation for virus particles. The sample clarification unit may, for example, include a total number of fluid containers in the sample clarification unit as described for the number of fluid containers that may be included in the sample purification unit.

The multi-sample processing units of the fourth aspect may include a sample filtration unit including a filter plate having a plurality of filter wells with filter medium (e.g., filter element) to filter a mixture comprising purified sample and a unit volume of the purification particles following processing in a fluid container of the sample purification unit. The sample filtration unit may also include a filtrate collection plate comprising a plurality of filtrate collection containers to receive filtrate passing through filter media of a filter well of the filter plate. The filtration unit may include a total number of the filter wells of any convenient number, for example any of the numbers described previously with respect to the number of fluid containers in the fluid purification unit. The filtration unit may include a total number of filter wells equal to a total number of fluid containers in the sample purification unit and/or equal to a total number of fluid containers in a sample clarification unit when the kit includes such a sample clarification unit. The filter media may be in the form of a porous filter material that allows filtrate to pass from an internal volume of the filter well to a corresponding filtrate collection container. Such porous material may, for example, be a porous metal, porous polymeric or porous ceramic material with a pore size and structure providing a desired size for filtration separation. The filter media may have a filtration separation size as discussed above in relation to the first or third aspects. In some preferred implementations of the fourth aspect, the filter media of each filter well may have a filtration separation size in a range having a lower limit of 0.1 micrometer, 0.2 micrometer, 0.3 micrometer, 0.4 micrometer, 0.5 micrometer or 0.7 micrometer and an upper limit of 2 micrometers, 1.5 micrometers or 1.3 micrometers. The filter media may, for example, be provided by a porous wall of a side or bottom of a filtration well, or may be a separate filter element structure supported by a supporting structure of the filter well. Each filter well may have a volume in a range having a lower limit of 10 microliters, 25 microliters, 100 microliters or 250 microliters and an upper limit of 15 milliliters, 10 milliliters, 5 milliliters, 2 milliliters or 1 milliliter or 500 microliters. Each filtrate collection container may have a fluid containment volume in a range having a lower limit of 25 microliters, 100 microliters, 250 microliters, 500 microliters or 750 microliters and an upper limit of 50 milliliters, 35 milliliters, 20 milliliters, 10 milliliters, 5 milliliters, 2 milliliters, or 1.5 milliliters.

Any one of more of a sample purification unit, sample clarification unit and sample filtration unit may each be individually packaged within the kit in separate sterile packaging enclosures. For example, a sample purification unit may be individually packaged in a first sterile packaging enclosure, a sample clarification unit may be individually packaged in a second sterile packaging enclosure and a sample filtration unit may be individually packaged in a third sterile packaging enclosure. The sterile packaging enclosure of any such multi-sample processing unit may, for example, include an enclosure of a metallic or polymeric film barrier material (e.g., in the form of a bag, pouch, wrapping, heat-sealed enclosure or other enclosure structure) or a package having a formed polymeric or metallic receptacle and a polymeric, metallic or cardboard backing material. The multi-sample processing units, and/or other components of the kit, may be all disposed within a single common packaging container, for example in a single common bag, box, wrapping or packaging container.

In addition to the aspects and features described above, further aspects and features will become apparent by reference to the drawings and by study of the following descriptions.

DETAILED DESCRIPTION OF SOME EXEMPLARY EMBODIMENTS

When reference is made to a multi-sample processing unit, the reference is to components of such a unit, whether assembled or not, and subassemblies including such components.

FIGS. 1-14 show generalized process block diagrams illustrating various example processing embodiments for a method of the first aspect. The processing shown in FIGS. 1-14 may be performed on a single sample of biological material in preparation of flow cytometry evaluation of that single processed sample or may be performed on a plurality of samples of biological material in preparation of flow cytometry evaluation on a plurality of a plurality of processed samples, for example in preparation of automatically feeding such a plurality of processed samples in sequence to a flow cytometer using an autosampler.

Figure 1:
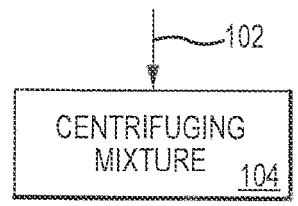
FIG. 1 shows a generalized process block diagram for some embodiments.

FIG. 1 shows a generalized process block diagram illustrating features for some embodiments. As shown in FIG. 1, a mixture 102, which includes biological material and purification particles, is subjected to centrifuging 104. Prior to the centrifuging 104, the materials of the mixture 102 may have been intimately contacted for a period of time sufficient to promote capture of smaller-size impurities in porous cores of the purification particles. Such intimate contact may have been promoted through agitation or mixing of the mixture 102 prior to the centrifuging 104. A result of the centrifuging 104 may be a centrifuged composition with density-separated phases that include a more-dense phase that is concentrated in the purification particles, relative to the mixture 102, and a less-dense supernatant. The less-dense supernatant may be concentrated, relative to the mixture 102, in one or more components of the biological material that are not captured within the purification particles, which may include larger-size components, which may include virus particles and particles larger than virus size, too large to pass through shells of the purification particles (too large to pass through pores of the shells) into the cores of the purification particles and/or smaller-size components not captured within the cores of the purification particles. Such supernatant may be recovered and some or all recovered supernatant, or components thereof, may be subjected to flow cytometry evaluation for the presence of virus after any desired intermediate processing between the centrifuging 104 and flow cytometry. Such intermediate processing may include, for example, one or more operations such as filtration, dilution, concentration, solute adjustment, pH adjustment or marking components with a fluorescent or other marker to aid detection and differentiation during flow cytometry. When processing a plurality of samples, the centrifuging 104 may include simultaneous centrifuging a plurality of such mixtures 102 with each such mixture 102 disposed in a different one of a plurality of fluid containers of a sample purification unit. The sample purification unit with such a plurality of such mixtures 102 may be placed in a centrifuge and centrifuged with the plurality of the mixtures 102 disposed therein.

Figure 2:
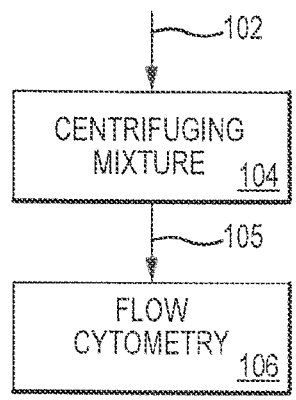
FIG. 2 shows a generalized process block diagram for some embodiments.

FIG. 2 shows a generalized process block diagram illustrating general processing in which a sample 105 including at least a portion of supernatant from the centrifuging 104 may be subjected to flow cytometry 106. The flow cytometry 106 may be directed to identifying and/or quantifying the presence of virus particles. By a portion of the supernatant, or of any composition, it is meant some material sourced from the source composition, which may or may not have the same compositional make-up as the original composition. When processing a plurality of samples, the flow cytometry may include sequentially feeding a plurality of such samples 105 resulting from the centrifuging 104 to a flow cytometer. Each of the plurality of such samples 105 may be removed, manually or automatically by an autosampler, from the respective container and fed, manually or automatically by such an autosampler, the flow cytometer.

Figure 3:
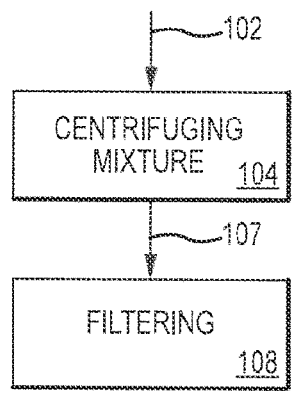
FIG. 3 shows a generalized process block diagram for some embodiments.

FIG. 3 shows a generalized process block diagram illustrating general processing in which a liquid-containing composition 107, including at least a portion of supernatant from the centrifuging 104, is subjected to filtering 108 to remove at least a portion, and in some instances at least a majority by mass or even substantially all, of larger-size components of the biological material that are larger than a virus size that may be present in the liquid-containing composition 107. The presence of such components larger than a virus size may interfere with effective flow cytometry evaluation for accurate identification and/or quantification of virus particles. Retentate from the filtering 108 may be concentrated, relative to the liquid-containing composition 107, in larger-size components of the biological material that are larger than virus particles and filtrate resulting from the filtering 108 may be concentrated, relative to the liquid-containing composition 107, in virus particles and in smaller-size components of the biological material that are smaller than virus particles. In some preferred embodiments, filtration during the filtering 108 may include centrifugal filtration. When processing a plurality of samples, the filtering 108 may include simultaneously filtering a plurality of such liquid-containing compositions 107 each including at least a portion of supernatant from processing a different mixture 102 in the centrifuging 104. Such filtering of a plurality of liquid-containing compositions 107 may include centrifuging the liquid-containing compositions in a multi-sample processing unit, such as a sample purification unit.

As one alternative to the general processing shown in FIG. 3, the centrifuging 104 may be performed with the mixture 102 in a container assembly that includes a centrifugal filter, in which case the mixture 102 may be subjected to both density separation and centrifugal filtration during the centrifuging 104 with at least a portion of the supernatant recovered in the form of filtrate that passes through a centrifugal filter element during the centrifuging 104, from which at least a portion of the larger-size components are removed by filtration during the centrifuging 104.

Figure 4:
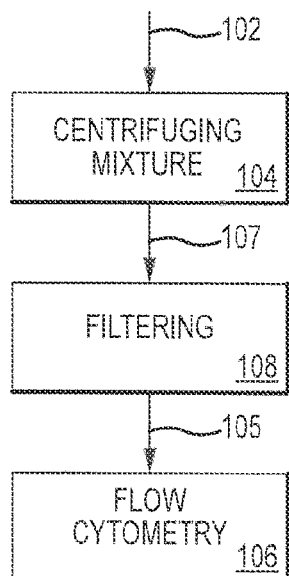
FIG. 4 shows a generalized process block diagram for some embodiments.

FIG. 4 shows a generalized process block diagram that includes the same general processing as shown in FIG. 3, except showing the sample 105, including at least a portion of filtrate from the filtering 108, being subjected to the flow cytometry 106 for evaluation for the presence of virus particles.

Figure 5:
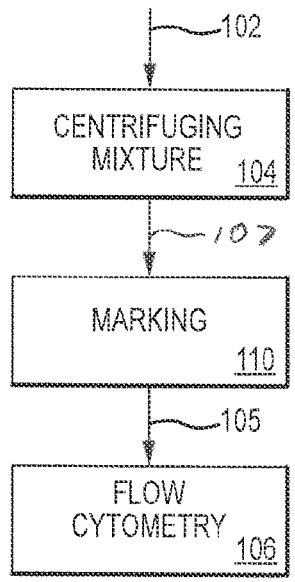
FIG. 5 shows a generalized process document for some embodiments.

FIG. 5 shows a generalized process block diagram in which at least a portion of supernatant from the centrifuging 104 is subjected to marking 110 to prepare the sample 105 prior to flow cytometry 106. During the marking 110, one or more biological components may be marked with a marker to aid identification. Such a marker may, for example, be a fluorescent marker, such as a fluorescent dye or stain, that preferentially associates with one or more different components of biological material. During the marking 110, multiple markers may be used that preferentially associate with different biological components to prepare the sample 105. For example, a first marker may preferentially associate with one or more proteins and a second marker may preferentially associate with nucleic acids, for example as disclosed in U.S. Patent Application Publication No. 2012/0070818, the entire contents of which are incorporated herein by reference. Such selective marking of biological material components may assist in more accurate identification and differentiation of virus particles during the flow cytometry 106. When processing a plurality of samples, each of a plurality of fluorescently marked samples 105 may be prepare in multiple fluid containers of a multi-sample processing unit, such as for example in filtrate collection containers of a sample filtration unit.

Figure 6:
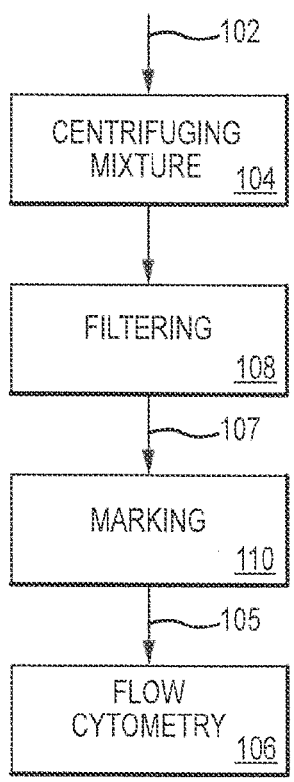
FIG. 6 shows a generalized process block document for some embodiments.

FIG. 6 shows a generalized process block diagram including the same general processing as shown in FIG. 5, except also showing the filtering 108 being performed prior to the marking 110. As one alternative to the processing order shown in FIG. 5, the marking 110 could be performed before the filtering 108.

FIGS. 2-6, just discussed, illustrate some example processing that may occur in some embodiments after the centrifuging 104. Reference is now made to FIGS. 7-14, which illustrate some example processing that may occur in some embodiments prior to the centrifuging 104.

Figure 7:
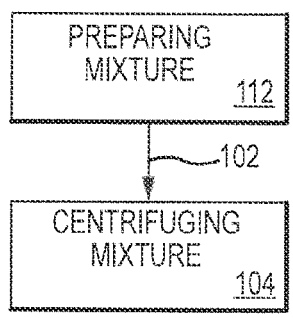
FIG. 7 shows a generalized process block diagram for some embodiments.

FIG. 7 shows a generalized process block diagram including a step of preparing 112 the mixture 102 prior to the centrifuging 104. The preparing 112 may include any preliminary processing involved with providing or making the mixture 102. When processing a plurality of samples, the preparing 112 may include preliminary processing for providing or making a plurality of such mixtures 102, for example with processing in one or more multi-sample processing units.

Figure 8:
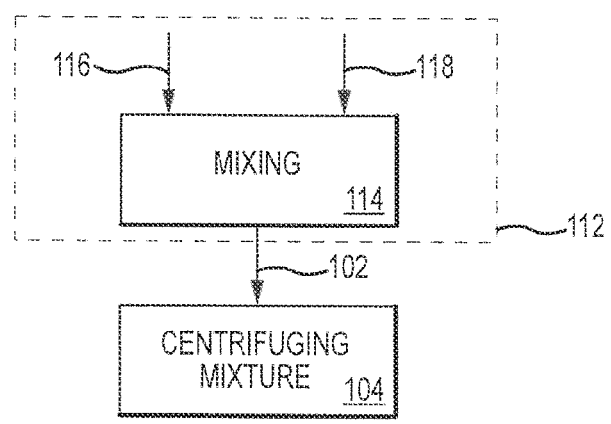
FIG. 8 shows a generalized process block diagram for some embodiments.

FIG. 8 shows the same generalized processing as shown in FIG. 7, except that in embodiments of FIG. 8 the preparing 112 includes a step of mixing 114 to prepare the mixture 102 or a precursor for the mixture 102. The mixing 114 includes mixing ingredients including at least biological material 116 and purification particles 118. Other ingredients may also be fed to the mixing for inclusion in the mixture 102 as desired. For example, a buffer solution may be added to adjust solute concentrations and impart a desired pH or other properties to the mixture 102, for example to promote effective capture of smaller-size impurities within cores of the purification particles 118 and/or for subsequent flow cytometry that may be performed after the centrifuging 104. When processing a plurality of samples, such mixing 114 may be performed with multiple input pairs of a quantity of biological material and corresponding quantity of purification particles to prepare a plurality of such mixtures 102 for processing in the centrifuging 104. As an example, such mixing 114 may be performed in multiple fluid containers of a multi-sample processing unit, which may for example be a fluid containers of a sample purification unit.

Figure 9:
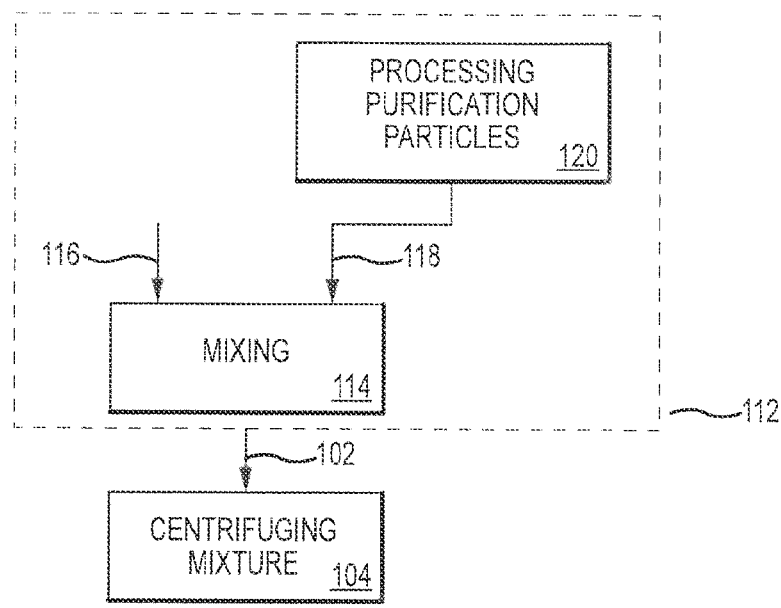
FIG. 9 shows a generalized process block diagram for some embodiments.

FIG. 9 illustrates other processing alternatives for use in some embodiments of the preparing 112 within the more generalized processing of FIG. 7. As shown in FIG. 9, the preparing 112 may include processing purification particles 120, which may include any preliminary processing of purification particles to provide or put the purification particles 118 in a form desired for use in the mixing 114. In some embodiments, purification particles may be provided in a sealed container containing a unit quantity of the purification particles required to prepare a single batch of the mixture 102 corresponding with a single sample at biological material 116 for evaluation. The processing purification particles 120 may include unsealing such a sealed container and removing the purification particles from the sealed container for introduction to the mixing 114, or the mixing may be performed while the purification particles remain in the container. In some embodiments, the sealed container may contain the purification particles mixed with a storage liquid and the purification particles and storage liquid may be centrifuged to prepare a centrifuged composition with density-separated phases, from which at least a portion of the storage liquid may be removed as supernatant. Following such removal of storage liquid, the purification particles 118 may then be fed to the mixing 114 for combination with other ingredients during the mixing 114. When processing multiple samples, the processing purification particles 120 may be performed on multiple batches of purification particles that may each include a unit quantity of purification particles for processing with one of a plurality of samples of biological material being processed, to prepare a plurality of batches of such purification particles 118. Such processing purification particles may include unsealing a plurality of sealed containers each containing such a batch of purification particles and a quantity of storage liquid. Such plurality of sealed containers may be in the form of sealed fluid containers of a sample purification unit, and the sample purification unit may be centrifuged to prepare a plurality of such centrifuges compositions. Such centrifuging a sample purification unit may be performed before or after unsealing such sealed containers.

Figure 10:
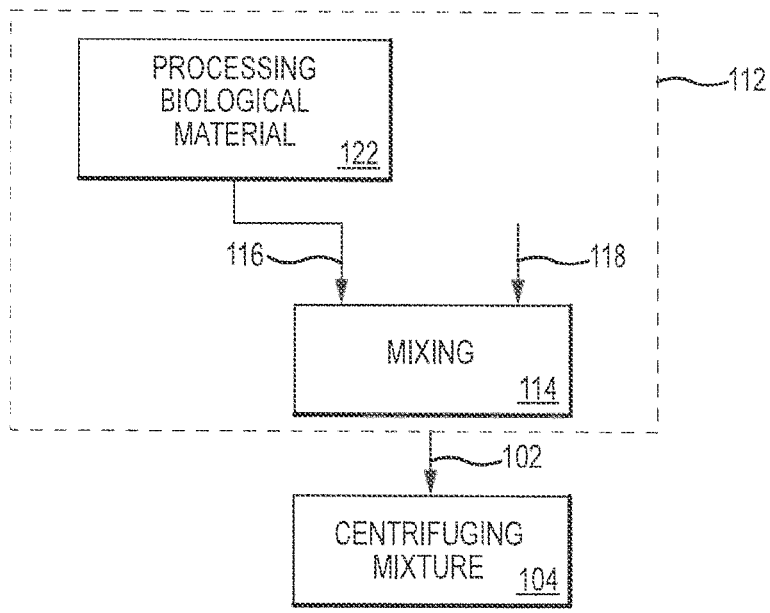
FIG. 10 shows a generalized process block diagram for some embodiments.

FIG. 10 illustrates other processing alternatives for use in some embodiments of the preparing 112 within the context of the generalized processing of FIG. 7. As shown in FIG. 10, the preparing 112 may include processing biological material 122, which may include preliminary processing to provide or put the biological material 116 in a form desired for use in the mixing 114. Such preliminary processing may include partial purification or adjustment of properties of a biological material sample prior to the mixing 114. For example, biological material to be evaluated may be provided initially in a crude biological material sample. Such a crude biological material sample may be diluted with a buffer solution and subjected to centrifuging. The biological material 116 used in the mixing 114 may include a portion of supernatant from such centrifuging, which may be at least partially cleaned of particles and cellular material that may form a dense pellet during the centrifuging. When processing multiple samples, the processing biological material 122 may include processing a plurality of feed batches, or samples, of biological material to be evaluated to prepare a plurality of batches of such biological materials 116 for use in the mixing 114. For example, the processing biological material may include diluting each of a plurality of crude biological material samples with a buffer solution and subject all diluted samples to centrifuging. For example, such diluting may be accomplished by adding such a sample of crude biological material to a different one of a plurality of fluid containers of a sample clarification unit, wherein such fluid containers may be prefilled with an appropriate quantity of such buffer solution for processing a single such crude biological material sample.

Figure 11:
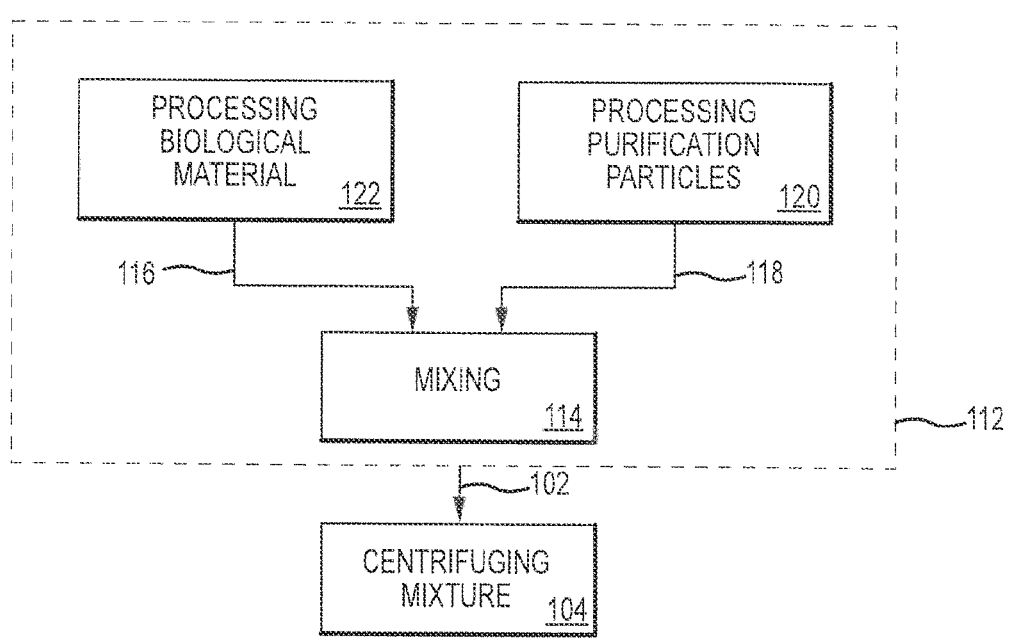
FIG. 11 shows a generalized process block diagram for some embodiments.

FIG. 11 illustrates other process alternatives for some embodiments of the preparing 112 within the more generalized processing of FIG. 7. As shown in FIG. 11, the preparing 112 may include both the processing biological material 122 and the processing purification particles 120, such as shown individually in FIGS. 9 and 10 and discussed above.

Figure 12:
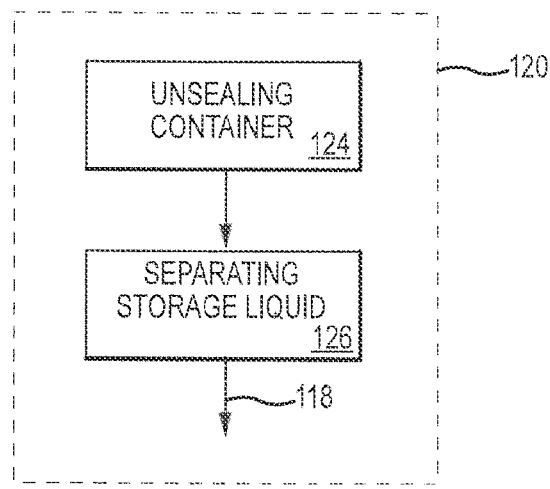
FIG. 12 shows a generalized process block diagram for some embodiments.

FIG. 12 illustrates some preliminary processing that may be performed in some embodiments during the processing purification particles 120 shown in FIGS. 9 and 11. As shown in FIG. 12, the processing purification particles 120 may include a step of unsealing 124 a sealed container in which the purification particles may initially be disposed. The purification particles may be present in the sealed container in a pre-prepared unit quantity of the purification particles for use to prepare a single batch of the mixture 102 for evaluation of a single sample of the biological material 116. The purification particles in the sealed container may be mixed with a storage liquid. As shown in FIG. 12, the processing purification particles 120 may include a step of separating 126 to separate at least a portion of storage liquid from purification particles to prepare the purification particles 118 free of at least a portion of the storage liquid or even free of a majority or of substantially all of the storage liquid. The separating 126 may include any liquid-solid separation technique, for example filtration or density separation. When processing a plurality of samples, such liquid-solid separation may be performed on a plurality of separate mixtures of purification particles and storage liquid, for example by centrifuging a sample purification unit with multiple fluid containers each including a such a mixture of purification particles and storage liquid. As an alternative to the processing shown in FIG. 12, such centrifuging cold be performed prior to unsealing such fluid containers, which could then be unsealed following the centrifuging to remove supernatant of storage liquid from each such fluid container.

Figure 13:
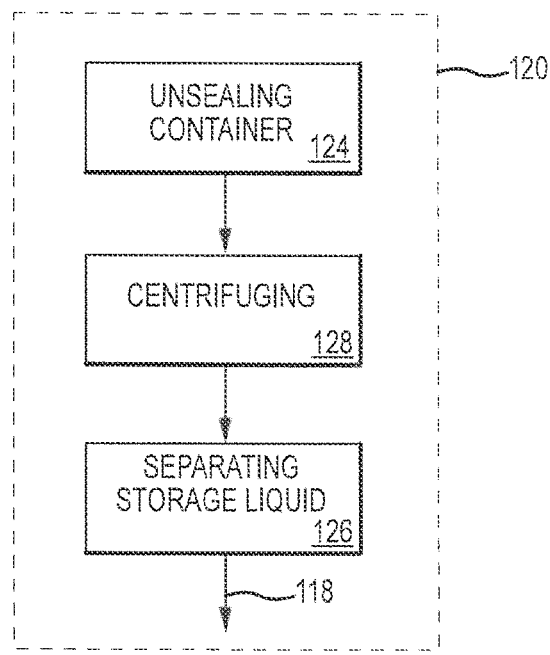
FIG. 13 shows a generalized process block diagram for some embodiments.

FIG. 13 illustrates a more specific processing alternative for some embodiments within the more generalized processing of FIG. 12. As shown in FIG. 13, a mixture of purification particles and storage liquid may be subjected to centrifuging 128 following the unsealing 124 and prior to the separating 126. Following the centrifuging 128, at least a portion of the storage liquid in the form of supernatant may be removed from above centrifuged purification particles during the separating 126. When processing a plurality of samples, processing may for example be as described with respect to FIG. 12, with the separating storage liquid 118 being performed for example on each of the fluid containers of a sample purification unit following the centrifuging 104.

Figure 14:
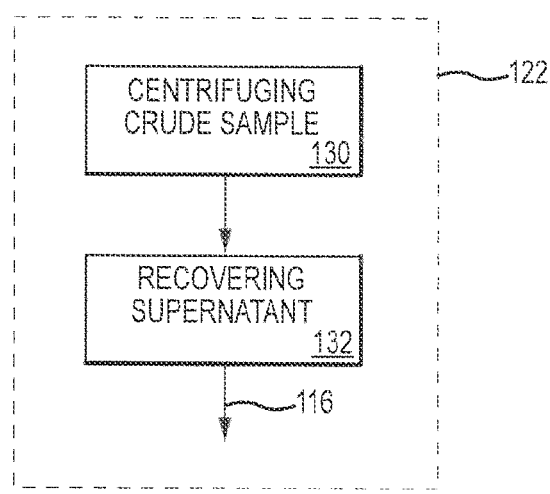
FIG. 14 shows a generalized process block diagram for some embodiments.

FIG. 14 illustrates some example preliminary processing that may be performed in some embodiments during the processing biological material 122, shown in FIGS. 10 and 11. As shown in FIG. 14, the processing biological material 122 may include a step of centrifuging 130 to centrifuge a crude sample of biological material, followed by a recovering 132 step to recover at least a portion of resulting supernatant that may then be used as or to prepare the biological material 116 for use in the mixing 114 of FIGS. 8-11. Prior to the centrifuging 130, such a crude sample of biological material may be mixed with buffer solution to dilute the crude sample and/or modify the chemical characteristics of the crude sample in preparation for the centrifuging step 130 or for subsequent processing. Particles and cellular material from the crude biological material sample may collect as a dense pellet during the centrifuging 130 from which supernatant may be separated during the recovering 132. When processing a plurality of samples, processing may be for example as described with respect to FIG. 10, with the recovering supernatant 132 performed on each of a plurality of fluid containers of a sample clarification unit.

Figure 15:
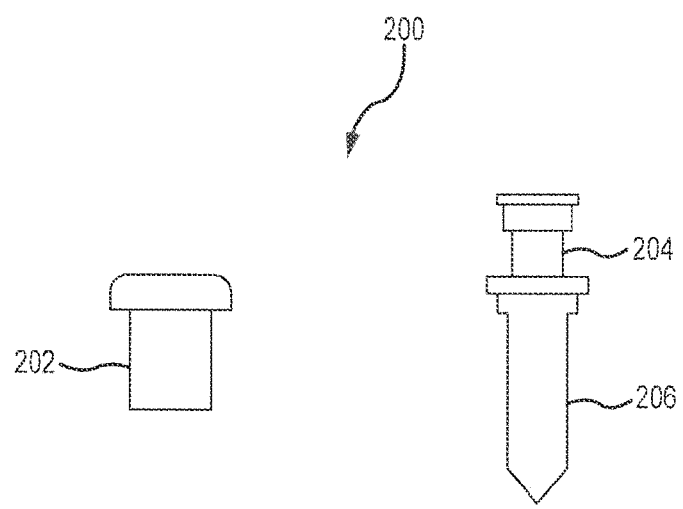
FIG. 15 illustrates components that may be included in a kit according to some embodiments.

FIG. 15 illustrates some embodiments of components of a kit. As illustrated in FIG. 15, a kit 200 may include a sealed container 202 and a centrifugal filter 204. As shown in FIG. 15, the centrifugal filter 204 may be insertable into a collection receptacle 206 for collecting filtrate passing through a filter element of the centrifugal filter 204 during a centrifugal filtration operation. The centrifugal filter 204 may include a filter element of a desired pore size and the collection receptacle 206 may have sufficient volume to collect a desired volume of filtrate during a centrifugal filtration operation. As an alternative to the illustration shown in FIG. 15, a kit could include the centrifugal filter 204 and not the collection receptacle 206. The sealed container 202 may include a unit quantity of purification particles for processing a single sample of biological material for flow cytometry evaluation for virus particles. The unit quantity of purification particles may be mixed with a storage liquid also contained within the sealed container 202. Such a sealed container 202 could be provided as a product separate from a kit including a centrifugal filter.

Figure 16:
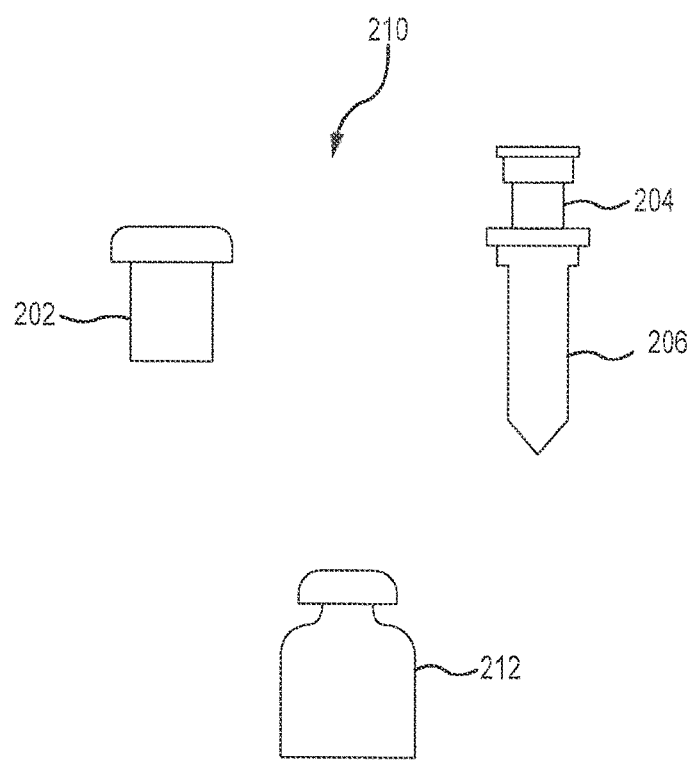
FIG. 16 illustrates components that may be included in a kit according to some embodiments.

FIG. 16 illustrates an example kit 210 including the sealed container 202, centrifugal filter 204 and collection receptacle 206 as illustrated in FIG. 15, and also including a second sealed container 212 containing buffer solution reagent. The second sealed container 212 may include the buffer solution reagent of a type and in a premeasured quantity for mixture with a unit quantity of purification particles in the scaled container 202 for processing a single sample of biological material for evaluation. The kit 200 or kit 210 may include multiple ones of such a sealed container 202, centrifugal filter 204 and/or collection receptacle 206 to facilitate processing more than a single sample of biological material. Likewise the sealed container 212 may include sufficient buffer solution to process more than one sample of biological material and/or the kit 201 may include multiple ones of such sealed containers 212.

Reference is now made to FIGS. 17-28 in relation to an example kit including a plurality of multi-sample processing units.

Figure 17:
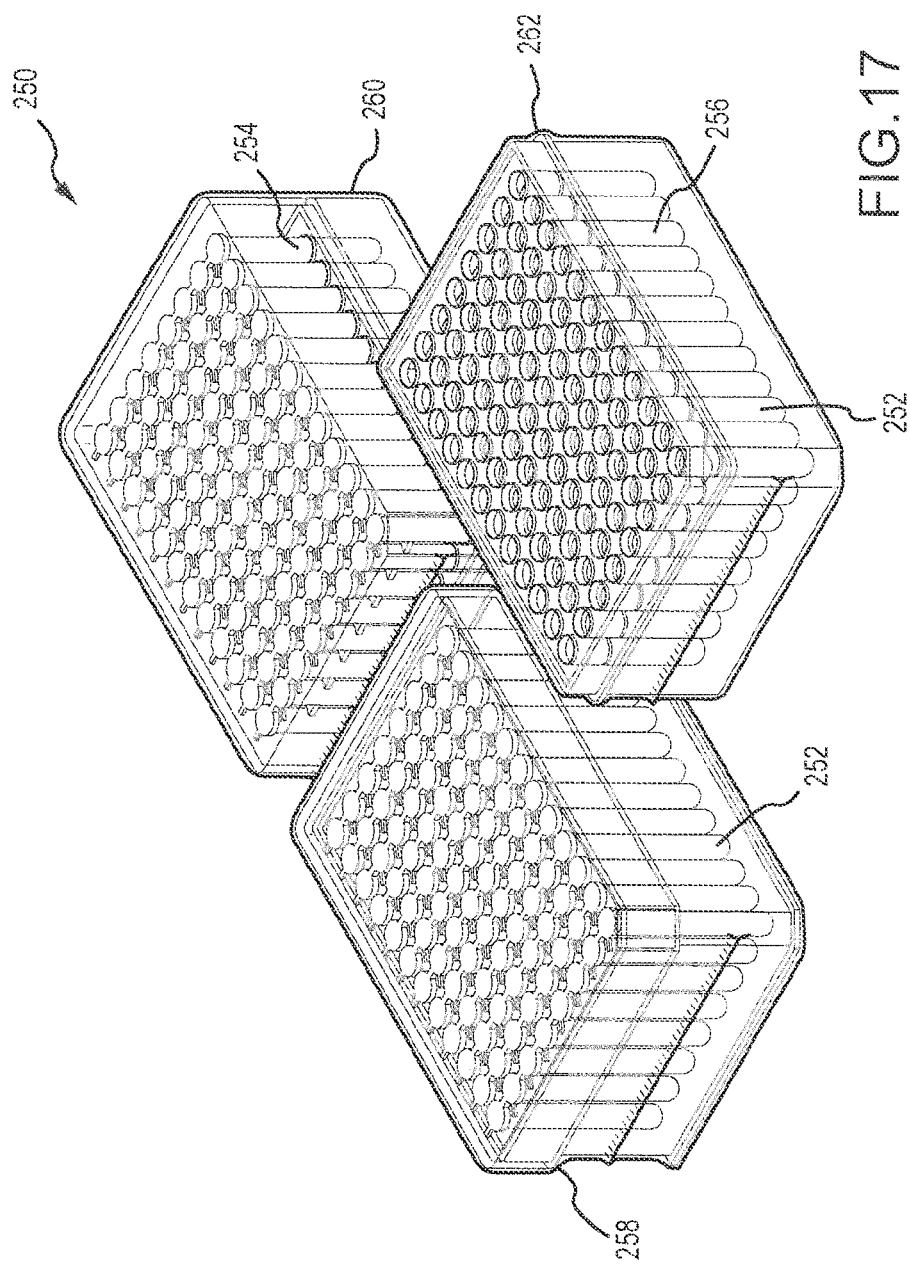
FIG. 17 illustrate an example embodiment of a kit including multi-sample processing units for processing a plurality of samples or biological material in preparation for flow cytometry evaluation.

FIG. 17 illustrates an example kit 250 including three multi-sample processing units, namely a sample clarification unit 252, a sample purification unit 254 and a sample filtration unit 256. Each of these multi-sample processing units is packaged individually in sterile packaging enclosures 258, 260 and 256, respectively, illustrated in the form of sealed plastic film barrier packaging. The multi-sample processing units may be further packaged together within a single common packaging container, for example in a common bag, box, wrapping, or packaging container.

Figure 18:
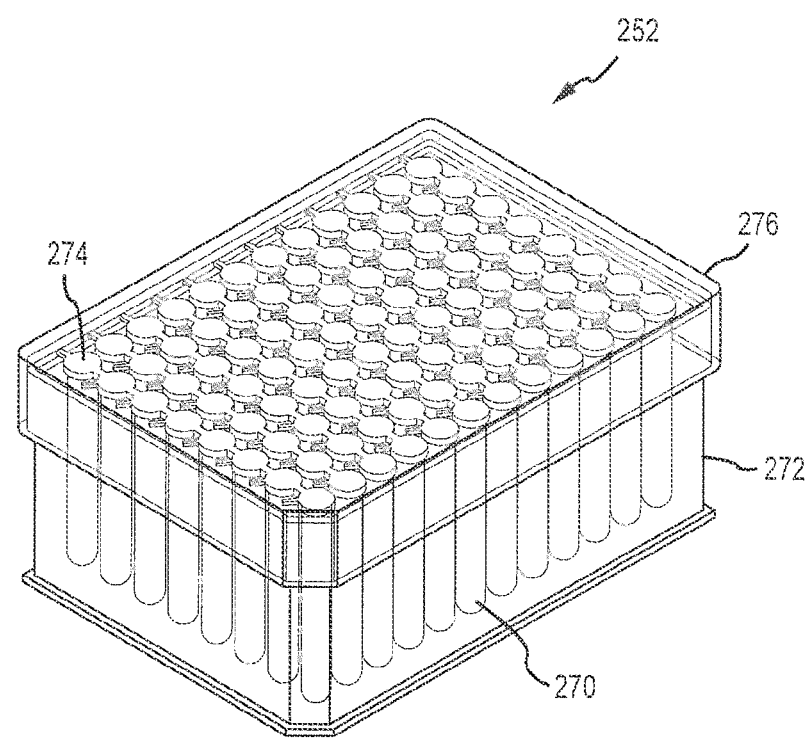
FIGS. 18-20 illustrate an example embodiment of a sample clarification unit.
Figure 19:
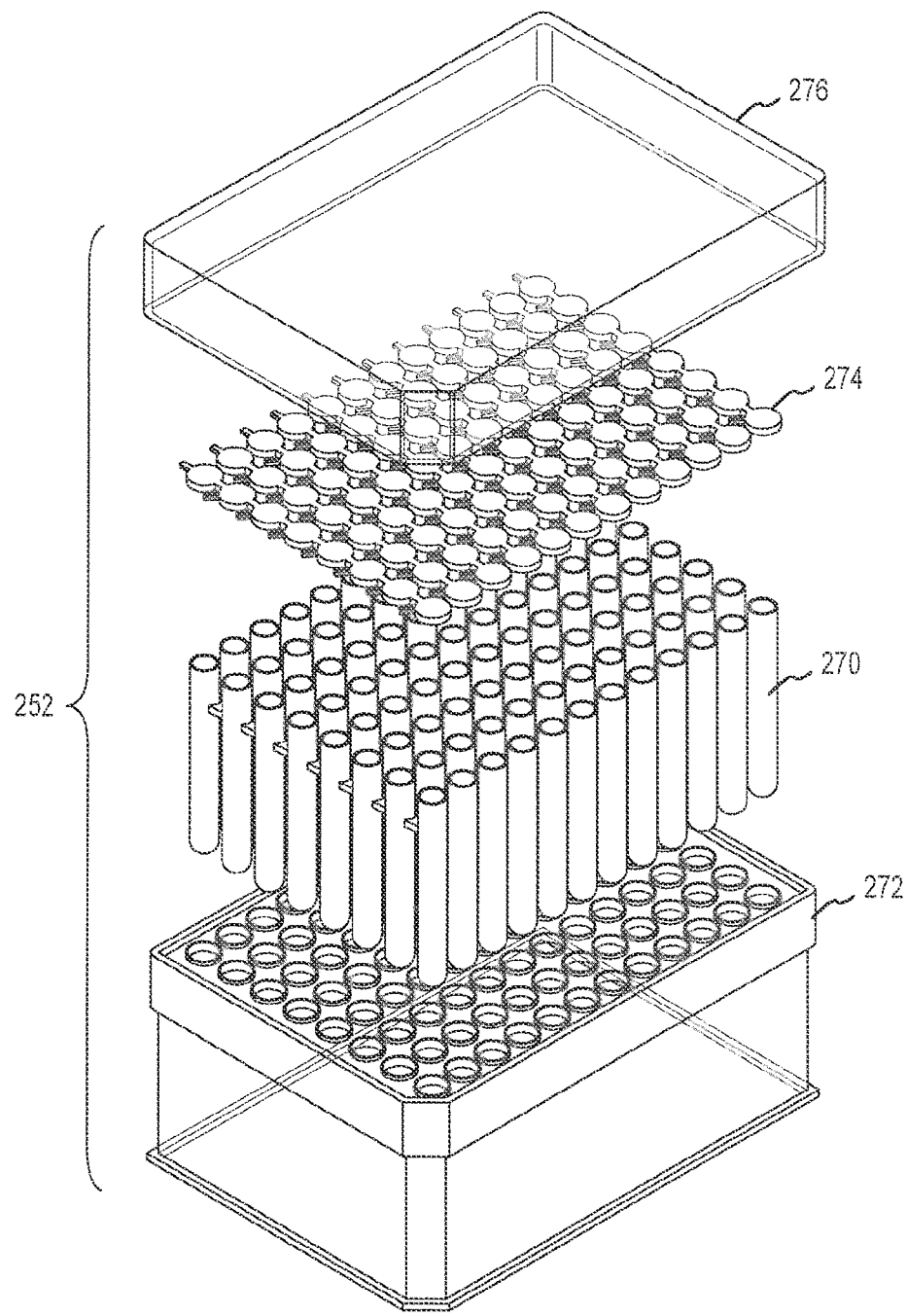
Figure 20:
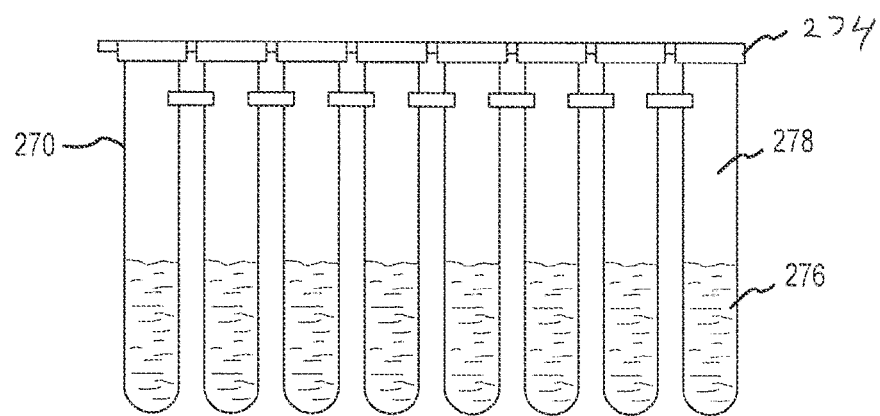

Reference is now made to FIGS. 18-20 in relation to the sample clarification unit 252. FIG. 18 illustrates the sample clarification unit 252 as assembled and FIG. 19 illustrates components of the sample clarification unit 252 in an exploded view. As shown FIGS. 18 and 19, the sample clarification unit 252 includes a plurality of fluid containers in the form of tubes 270 that may be received in corresponding receptacles of a rack 272. The sample clarification unit 252 also includes a plurality of caps 274 that may cap the tubes 270 to provide a seal to the fluid containment volume within the tubes 270. The sample clarification unit 252 also includes a cover 276 that mates with the rack 272 to protectively cover the tubes 270 as received within the rack 272. As illustrated in FIGS. 18 and 19, the example embodiment of the sample clarification unit 252 that is shown includes 96 tubes comprised of twelve 8-tube strips, although variations could include any desired number of such tubes 270. Correspondingly, in the example embodiment shown, the caps 274 are provided in a plurality of cap strips, with each cap strip including 8 caps, for illustration purposes, with each cap strip corresponding with a tube strip.

Figure 21:
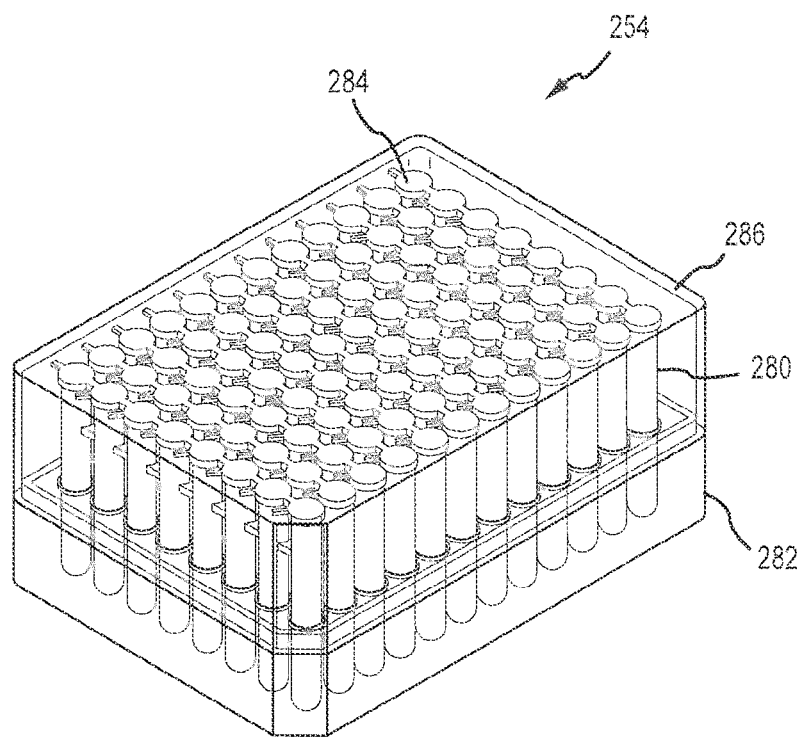
FIGS. 21-23 illustrate an example embodiment of a sample purification unit.

The sample clarification unit 252 includes buffer solution reagent disposed within the fluid containment volume of each of the tubes 270. FIG. 20 shows one of the tube strips containing a plurality of the tubes 270 with the tubes 270 capped by a cap 274 of a cap strip. As shown in FIG. 21 a volume of buffer solution reagent 276 occupies a first portion of the fluid containment volume of each of the tubes 270. A second portion 278 of such fluid containment volume is an unfilled volume within each of the tubes 270 that is available to receive a sample of biological material to mix with the buffer solution reagent 276, such as for sample clarification processing, for example pursuant to processing biological material 122 as shown in any of FIGS. 9, 10 and 14. The buffer solution reagent may be a buffer solution, for example a Tris-HCl buffer solution, for example as previously described.

Figure 22:
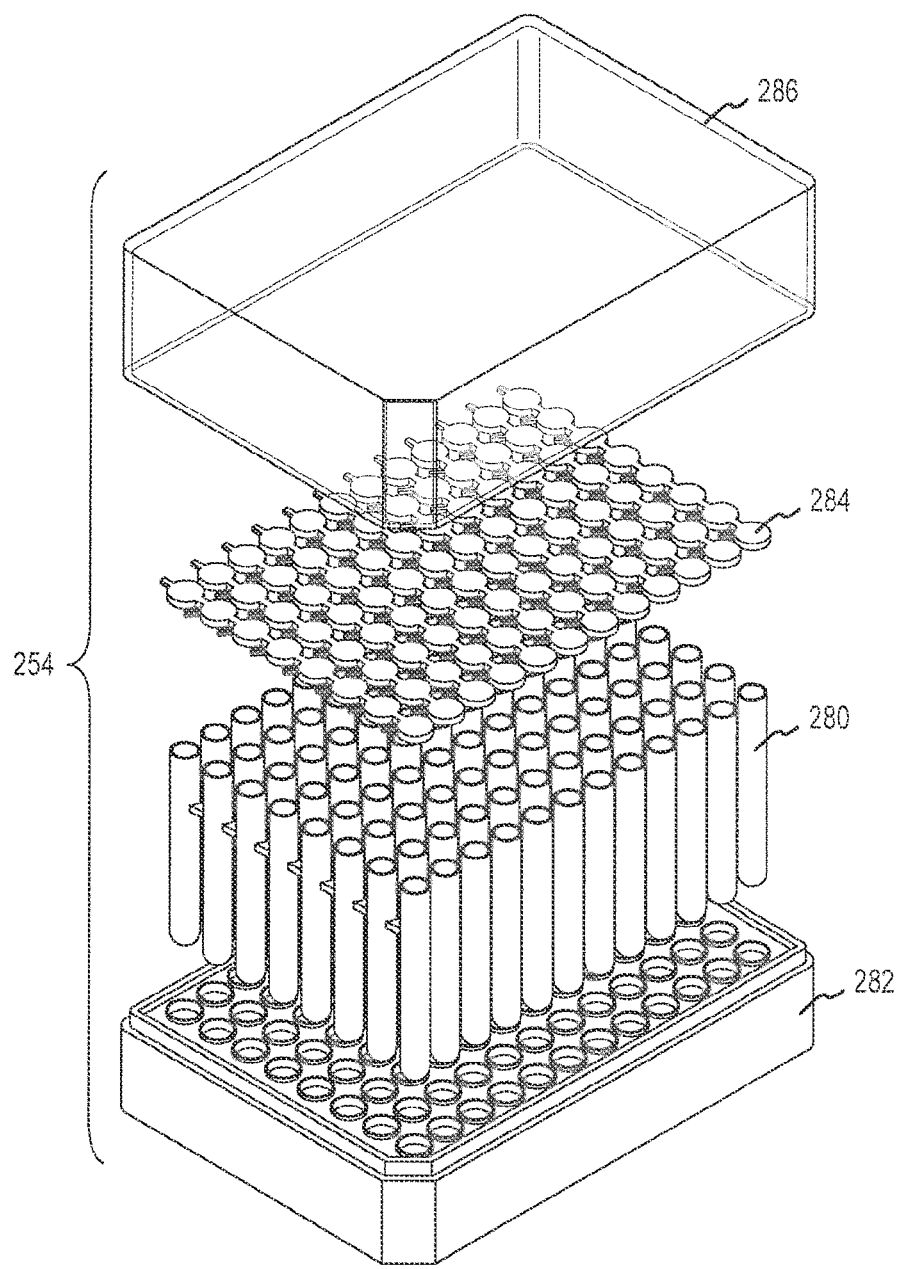
Figure 23:
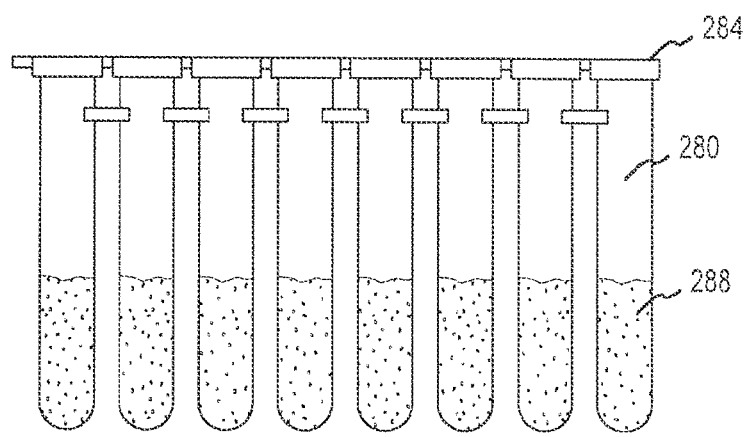

Reference is now made to FIGS. 21-23 in relation to the sample purification unit 254. FIG. 21 shows the sample purification unit 254 as assembled and FIG. 22 shows the components of the sample clarification unit 254 in exploded view. As shown in FIGS. 21 and 22, the sample purification unit 254 includes a plurality of fluid containers provided in the form of tubes 280, which may be received within receptacles of a rack 282. The fluid containment volume within the tubes 280 may be sealed with caps 284 to seal the fluid containment volumes within the tubes 280. The fluid purification unit 254 includes a cover 286 that mates with the rack to cover the tubes 280 received within the receptacles of the rack 282. The fluid purification unit 254 has components and an assembly construction similar to that of the fluid clarification unit 254, and the tubes 280 and caps 284 of the sample purification unit 254 are provided in the form tube strips and corresponding cap strips in a manner as described with respect to the sample clarification unit 252. The tubes 280 each have disposed therein a volume of a mixture comprising a unit quantity of purification particles and buffer solution storage liquid. The purification particles may, for example, be as described above, and may comprise a porous core functionalized capture at least some non-virus impurities and a porous size exclusion cell surrounding the core and having a pore structure to exclude larger-sized components from entering into the core through the pore structure of the shell while permitting the smaller-size components to enter into the core through the pore structure of the shell. The storage liquid may be a buffer solution, which may be a Tris-HCl buffer solution, for example as described above. The bulk volume of purification particles, volume of buffer solution storage liquid and ratio of volume of buffer solution storage liquid to bulk volume of purification particles may be, for example, as described above. The total containment volume within each tube may be larger than the bulk volume of the purification particles, for example as described above, to provide volume to receive clarified sample of biological material for further purification processing of the sample. FIG. 23 shows one example tube strip of the tubes 282 and a corresponding cap strip of the caps 284 of the sample purification unit 254. As shown in FIG. 23, each of the tubes 280 includes a mixture including purification particles and storage liquid disposed in a fluid containment volume of each tube 280.

Figure 24:
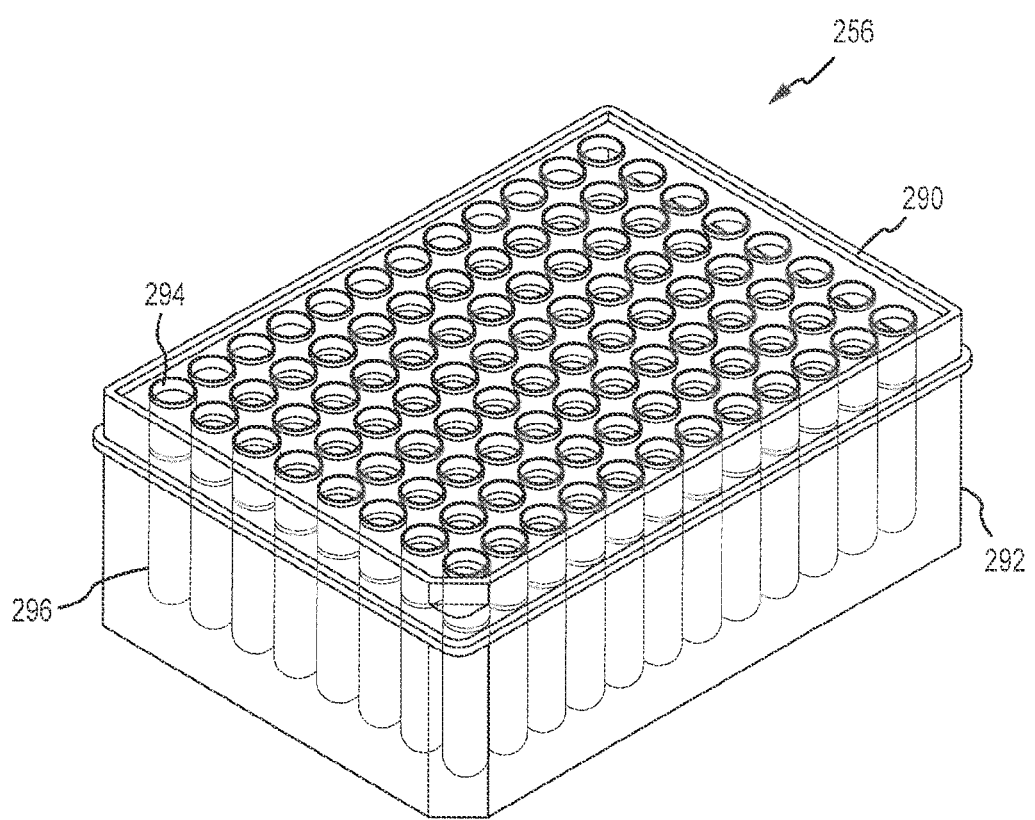
FIGS. 24-28 illustrate an example embodiment of a sample filtration unit and use thereof for centrifugal filtration.
Figure 25:
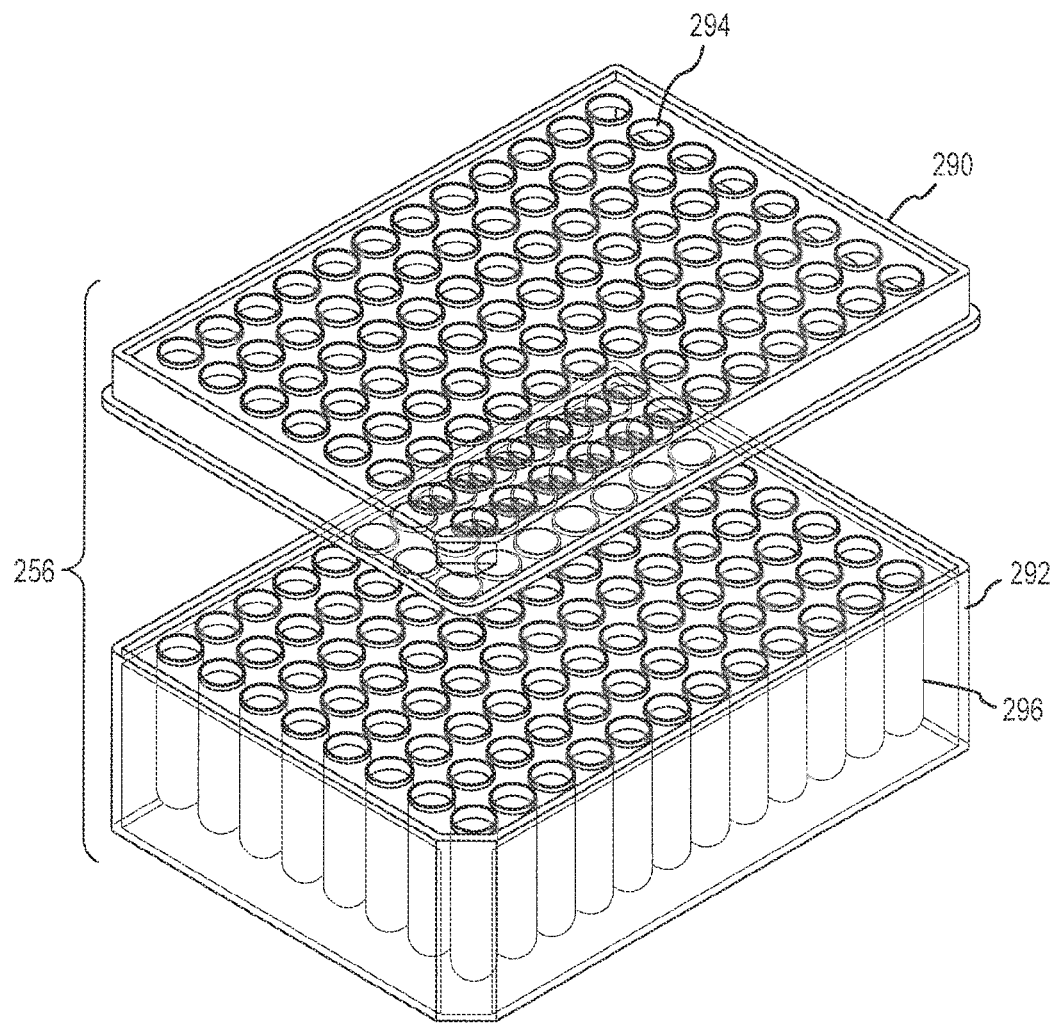
Figure 26:
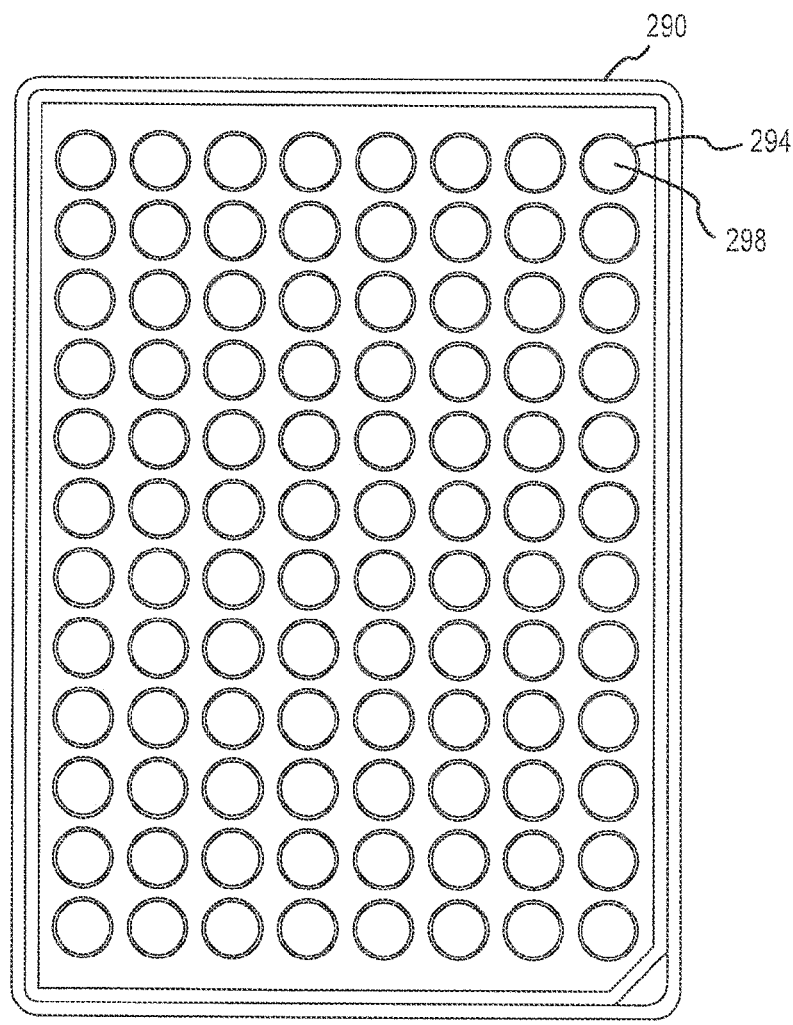

Reference is now made to FIGS. 24-28 in relation to the sample filtration unit 256. FIG. 24 shows the sample filtration unit 256 assembled and FIG. 25 shows components of the sample filtration unit 256 in an exploded view. As shown in FIGS. 24 and 25, the sample filtration unit 256 includes a filter plate 290 and a filtrate collection plate 292. The filter plate 290 is shown by itself in FIG. 26. The filter plate 290 includes a plurality of filter wells 294 in which a mixture comprising purified sample and purification particles may be introduced for filtration processing, for example to remove the purification particles from liquid containing the purified sample in the mixture. The filter wells 294 include filter media through which filtrate may pass to be collected in filtrate collection containers 296 of the filtrate collection plate 292. As shown in FIGS. 24 and 25, the filtrate collection containers 296 may be in the form of fluid containment wells within the filtrate collection plate 292. Filter media of the filter wells 294 may be in the form of porous material forming a bottom and/or side wall of the filter wells 294, for example such porous material may be a porous metallic, polymeric or ceramic material. FIG. 26 shows porous filter media 298 disposed at a bottom of the filter wells 294, to permit filtrate to pass through the bottom of a filter well 294 into a corresponding filtrate collection container 296.

Figure 27:
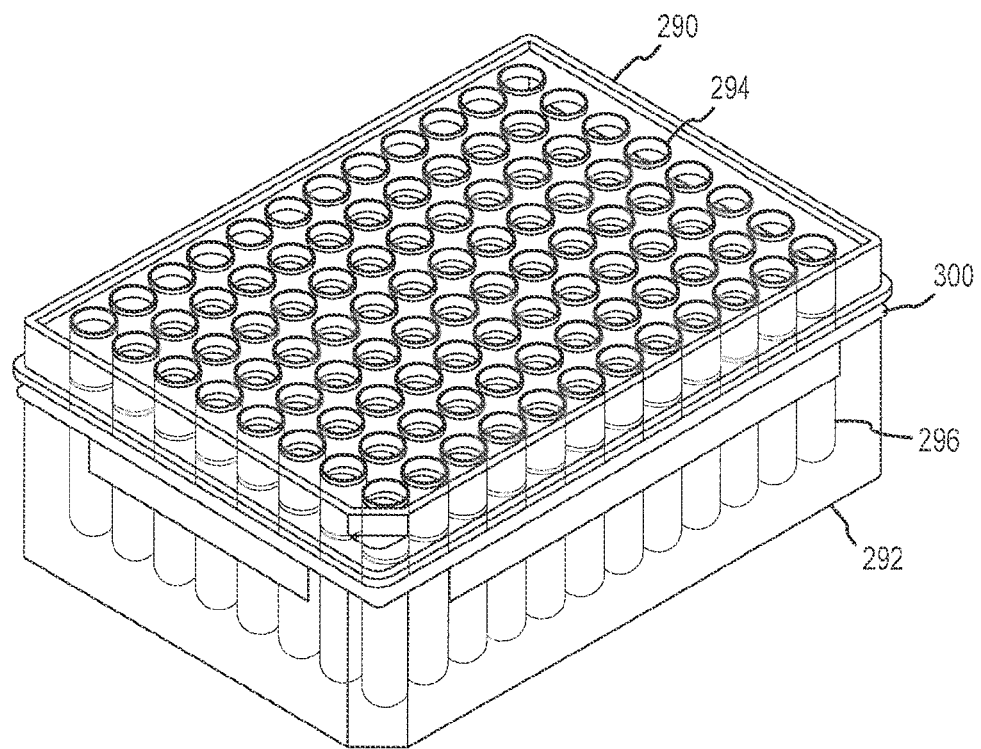
Figure 28:
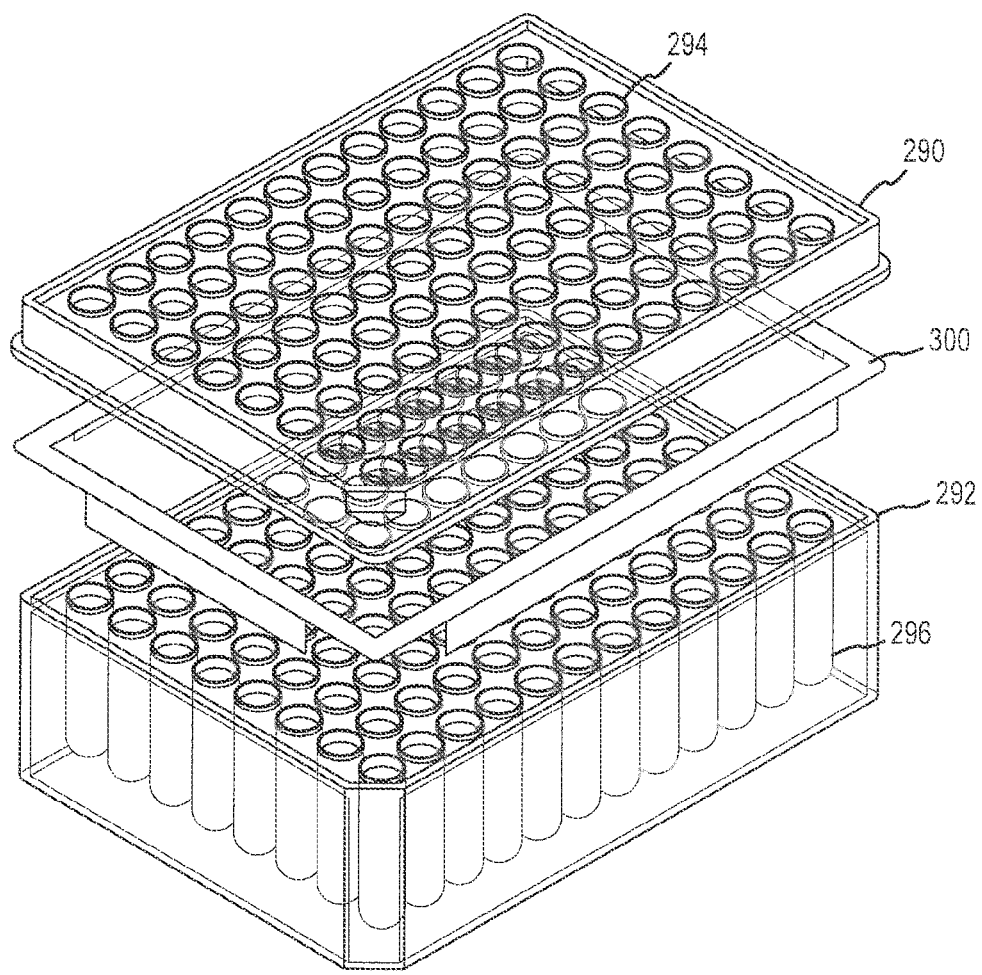

The sample filtration unit 256 may be centrifuged to effect simultaneous centrifugal filtration of a plurality of mixtures introduced into the filtration wells 294 and to cause collection of filtrate in the corresponding filtrate collection containers 296. Reference is made to FIGS. 27 and 28 showing an example preparation of the filter unit 256 for centrifuge processing. As shown in FIGS. 27 and 28, for centrifuge processing of the sample filtration unit 256, a collar 300 is disposed between the filter plate 290 and the filtrate collection plate 292 of the sample filtration unit 256. The collar may be of a metallic material and may helps to prevent the filter plate 290 from being forced into the filtration collection plate 292 during the centrifuging in a manner that may damage one or both of the filter plate 290 and the filtration collection plate 292 during the centrifugal filtration.

EXAMPLES

Example 1

A specific example is provided of processing a single sample of biological material in preparation for flow cytometry evaluation. Materials for the example are shown in Table 1.

TABLE 1

| | |
|---|---|
| Capto ™ Core 700 purification particles | GE Healthcare, #17-5481-03 |
| 1× Tris/HCl Buffer Solution storage liquid | 12.5 mM Tris/HCl + 50 mM NaCl + 50 uM Zwittergent 3-14 + 0.05% sodium azide, pH = 8.0, 0.02 μm filtered |
| 10× Tris/HCl Buffer Solution reagent | 125 mM Tris/HCl + 500 mM NaCl + 500 μM Zwittergent 3-14 + 0.5% sodium azide, pH = 8.0, 0.02 μm filtered |
| Centrifugal Filter and accompanying collection tube | 0.8 μm VivaClear centrifugal filter, Sartorius Stedim #VK01P042 |
| Sealed container (2 mL sterile screw cap tube and cap) containing 700 μL mixture of 350 μL bulk volume of the purification particles and balance of the 1× Tris/HCl Buffer Solution storage liquid | |
| Crude sample of egg allantoic fluid containing influenza virus | |

The example includes the following processing:
Sample Preliminary Processing 1.1. Remove crude allantoic fluid/influenza sample from −80° C. freezer and let thaw to room temperature, or use fresh sample.

1.2. Set a 1000 μL pipet to draw up 450 μL, and pipet sample up and down ten (10) times to homogenize.

1.3. Pipet 450 μL of homogenized sample into sterile 1.6 mL microcentrifuge tube, discard pipet tip.

1.4. Add 50 μL of 10× Tris/HCl Buffer Solution reagent into sample tube (original sample is diluted by 10%).

1.5. Set 1000 μL pipet to draw up 500 μL, and pipet sample up and down ten (10) times to homogenize.

1.6. Centrifuge sample solution for 5 min at 3000 RCF.

Purification Particle Preliminary Processing 2.1. Transfer mixture of purification particles and storage liquid to a 1.6 mL microcentrifuge tube and centrifuge for 1 min at 3000 RCF.

2.2. Remove excess buffer (350 μL) on top of slurry following the centrifugation, leaving 350 μL bulk volume of the purification particles.

Centrifuge Mixture of Purification Particles and Sample 3.1. Using a 1000 μL pipet, draw up 500 μL of supernatant from centrifuged sample in step 1.6, and add to the tube containing the purification particles.

3.2 Form homogeneous slurry with the sample and purification particles by shaking the tube back and forth several times.

3.3 Place tube containing slurry on rocker and agitate at ~100 rpm for 30 min.

3.4 Centrifuge solution for 1 min at 1000 RCF.

Filtration 4.1. Place a centrifugal filter in a corresponding collection tube.

4.2. Using a 1000 μL pipet, draw up 550 μL of supernatant from step 3.4 and transfer to the centrifugal filter.

4.3 Centrifuge spin the centrifugal filter and collection tube for 3 min at 1000 RCF; if all sample has not spun down into the collection tube, repeat.

Following step 4.3, the filtrate in the collection tube may be stained with one or more fluorescent markers and the filtrate may then be subjected to flow cytometry evaluation for presence of the influenza virus.

Example 2

A specific example is provided for processing a plurality of sample of biological materials in preparation for flow cytometry evaluation using a kit including the following individually packaged multi-sample processing units:

Sample clarification plate: similar to as shown in FIGS. 18-20, with 96 sealed 1.2 mL tubes in 8-tube strips prefilled with 125 μL of 2× Tris-HCl buffer solution reagent (pH 8.0, including 25 mM Tris, 100 mM NaCl, 100 μM Zwittergent 3-14 and 0.05% sodium azide).

Sample purification unit: similar to as shown in FIGS. 21-23, with 96 sealed 1.2 mL tubes in 8-tube strips prefilled with a mixture of 175 μL Capto™ Core 700 purification particles and 175 μL of 1× Tris-HCl buffer solution storage liquid (pH 8.0, including 12.5 mM Tris, 50 mM NaCl, 50 μM Zwittergent 3-14 and 0.05% sodium azide).

Sample filtration unit: similar to as shown in FIGS. 24-26, with 96-well filter plate and 96-well filtrate collection plate, with filter wells sized at 350 microliters and with a filter separation size of 1.2 micrometers (SUPOR® AcroPrep™ Filter Plate, Pall) and 96-well filtrate collection plate with 1.0 mL round-bottom wells (VWR).

The example is to process up to ninety-six 125 μL samples of crude sample of egg allantoic fluid containing influenza virus. Processing includes the following:

Sample Clarification

1. Remove sample clarification unit from package and remove cover to access tubes
2. Pull off cap strip from each strip of 8 tubes
3. Pipette 125 μL of sample into each tube to be used (up to 96 samples)
4. Mix sample and buffer in each tube by pipetting up and down
5. Cap each tube
6. Place sample clarification unit (without cover) in centrifuge opposite of the properly weighted balance plate.
7. Spin at 1,500 g for 10 minutes
8. Remove sample clarification unit from centrifuge and set aside
9. Empty balance plate for later use Sample Purification (to Remove Impurities)

1. Remove sample purification unit from package and remove cover to access tubes
2. Adjust the balance plate to properly match sample purification unit
3. Place sample purification unit (without cover) in centrifuge opposite of the properly weighted balance plate and spin for 1 min at 1,000 g to spin down CaptoCore resin
4. Empty balance plate for later use
5. Remove 175 μL of excess buffer from slurry in each tube, leaving 175 μL of CaptoCore resin in each tube
6. Pull off 250 μL of clarified sample from each sample-containing tube of the sample clarification unit add to a tube of sample purification unit containing CaptoCore resin 7. Cap tubes of sample purification unit
8. Remove tubes in use from rack of sample purification unit and manually shake to form a slurry between the clarified sample and the CaptoCore resin
9. After shaking, place tube strips with clarifies sample and CaptoCore resin on their sides and agitate at approximately 100 rpm on orbital shaker for 30 minutes
10. After 30 minutes, return tubes to rack of sample purification unit
11. Place sample purification unit in centrifuge opposite of the properly weighted balance plate and spin for 3 minutes at 1,000 g
12. Remove sample purification unit from centrifuge and set aside Sample Filtration
1. Open the sample filtration unit from the package and separate the filter plate and filtrate collection plate. First, place a properly-sized receiver collar on top of the filtrate collection plate, and then place the filter plate on top of the receiver collar.
2. Remove 250 μL of supernatant from each used tube of the sample purification plate and add to a filter well of the filter plate of the sample filtration unit
3. Place the sample filtration unit, with the receiver collar between the filter plate and filtrate collection plate in centrifuge opposite of the properly weighted balance plate
4. Centrifuge at 1,000 g for 5 minutes.
5. Remove assembly from the centrifuge Following the sample filtration processing, the filtrate samples collected in the wells of the filtrate collection plate are ready for flow cytometry analysis. The flow cytometry analysis may be performed using an autosampler to automatically remove and feed each filtrate sample from the wells of the filtrate collection plate to a flow cytometer in sequential manner until all filtrate samples have been processed.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible embodiments and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed variation may be combined in any combination with one or more of any other features of any other variation or variations, to the extent that the features are not necessarily technically compatible, and all such combinations are within the scope of the present invention. The description of a feature or features in a particular combination do not exclude the inclusion of an additional feature or features. Processing steps and sequencing are for illustration only, and such illustrations do not exclude inclusion of other steps or other sequencing of steps. Additional steps may be included between illustrated processing steps or before or after any illustrated processing step.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, the a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. A method for processing biological material for flow cytometry evaluation for virus particles, the method comprising:
   centrifuging a mixture comprising biological material for evaluation and purification particles to prepare a centrifuged composition including a more-dense phase concentrated in the purification particles and a less-dense supernatant, wherein the biological material comprises larger-size components and smaller-size components and the purification particles comprise:
      a porous core functionalized to capture at least some non-virus impurities of the smaller-size components; and
      a porous size-exclusion shell surrounding the core and having a pore structure to exclude the larger-size components from entering into the core through the pore structure of the shell while permitting the smaller-size components to enter into the core through the pore structure of the shell; and
   filtering a liquid-containing composition comprising at least a portion of the supernatant comprising at least a portion of the larger-size components, wherein retentate of the filtering includes at least a portion of the larger-size components from the liquid-containing composition and the filtering comprises filtration at a separation size to pass at least a portion of particles of virus size in the filtrate of the filtering.

2. A method according to claim 1, wherein the centrifuging a mixture comprises simultaneously centrifuging a plurality of said mixtures with each said mixture disposed in a different fluid container of a multi-container sample purification unit.

3. A method according to claim 1, wherein the filtering comprises simultaneous centrifugal filtration at a said separation size of no larger than 2 microns of a plurality of said liquid-containing compositions, each comprising at least a portion of a different said supernatant from the centrifuging a plurality of said mixtures, to prepare a plurality of said retentates with each said retentate retained in a different filter well of a sample filtration unit and to prepare a plurality of said filtrates with each said filtrate collected in a different filtrate collection container of the sample filtration unit.

4. A method according to claim 1, comprising flow cytometry evaluation for presence of virus particles of a sample comprising at least a portion of the filtrate; and
contacting the at least a portion of the filtrate with at least one fluorescent marker prior to the flow cytometry evaluation.

5. A method according to claim 4, wherein the flow cytometry evaluation comprises sequentially subjecting to flow cytometry each of a plurality of said samples with each said sample comprising at least a portion of a different one of a plurality of said filtrates prepared by simultaneously filtering a plurality of said liquid-containing compositions.

6. A method according to claim 5, wherein the sequentially subjecting to flow cytometry comprises sequentially removing said samples from a multi-container plate with an autosampler and delivering said samples from the autosampler to a flow cytometer.

7. A method according to claim 1, comprising preparing the mixture, the preparing the mixture comprising:
mixing together the biological material and the purification particles; and
prior to the mixing, unsealing a sealed container containing the purification particles mixed with a storage liquid, wherein the sealed container contains a unit quantity of the purification particles for the mixture.

8. A method according to claim 7, wherein:
the preparing the mixture comprises preparing a plurality of said mixtures with each said mixture disposed in a separate container of a multi-container sample purification unit; and
the unsealing comprises unsealing each of the said separate containers of the sample purification unit, wherein each of the said separate containers of the sample purification unit comprises a said unit quantity of said purification particles mixed with said storage liquid.

9. A method according to claim 7, comprising prior to the mixing:
centrifuging the unit quantity of the purification particles and storage liquid to prepare a centrifuged composition; and
separating at least a portion of the storage liquid from the centrifuged composition.

10. A method according to claim 7, wherein the storage liquid comprises a Tris-HCl buffer solution;
the preparing the mixture comprises mixing the biological material, the unit quantity of the purification particles and a buffer solution reagent, the buffer solution reagent comprising a Tris-HCl buffer solution reagent; and
the mixture has a pH in a range of from pH 7 to pH 9.

11. A method according to claim 10, wherein the preparing the mixture comprises processing the biological material, wherein the processing comprises:
centrifuging a composition comprising crude biological material sample comprising the biological material and diluted with buffer solution reagent comprising a Tris-HCl buffer solution; and
recovering at least a portion of resulting supernatant comprising the biological material for inclusion in the mixture.

12. A method according to claim 7, wherein the pore structure of the shell is configured with a size exclusion cutoff of not larger than 1,000,000 Daltons and the core is functionalized with a hydrophobic ligand having a positive charge.

13. A method according to claim 7, wherein the mixture comprises from 35 microliters to 70 milliliters bulk volume of the purification particles and from 45 microliters to 90 milliliters of the biological material.

14. A method according to claim 13, wherein the mixture comprises a ratio of bulk volume of the purification particles to volume of the biological material in a range of from 0.5:1 to 1:1.

15. A method according to claim 1, wherein:
the biological material comprises material from a chicken egg;
the non-virus impurities comprise protein and nucleic acid impurities; and
the larger-size components comprise a member selected from the group consisting of cell debris, chicken embryo debris, bacteria, protein aggregates, lipids, lipid assemblies, lipid-protein assemblies, lecithins, lipid-protein aggregates, liposomes, ribosomes, vesicles, protein-nucleic acid complexes and combinations thereof.

16. A method according to claim 1, wherein:
the method comprises preparing the mixture, comprising mixing the biological material, the purification particles and a buffer solution reagent having a pH in a range of from pH 7 to pH 9;
the supernatant is concentrated in the larger size components of the mixture; and
the preparing the mixture comprises, prior to the mixing:
unsealing a sealed container containing the purification particles mixed with a buffer storage liquid, wherein the sealed container contains a unit quantity of the purification particles for the mixing; and
centrifuging the unit quantity of the purification particles and storage liquid to prepare a centrifuged composition and removing at least a portion of the storage liquid from the centrifuged composition.

17. A method according to claim 16, wherein:
the centrifuging a mixture comprises simultaneously centrifuging a plurality of said mixtures with each said mixture disposed in a different fluid container of a multi-container sample purification unit;
the filtering comprises simultaneously filtering a plurality of said liquid-containing compositions, each comprising at least a portion of a different said supernatant from the centrifuging a plurality of said mixtures, to prepare a plurality of said retentates with each said retentate retained in a different filter well of a sample filtration unit and to prepare a plurality of said filtrates with each said filtrate collected in a different filtrate collection container of the sample filtration unit;

the preparing, a mixture comprises preparing the plurality of said mixtures with each said mixture disposed in a separate container of the multi-container sample purification unit; and the unsealing comprises unsealing each of the said separate containers of the sample purification unit, wherein each of the said separate containers of the sample purification unit comprises a said unit quantity of said purification particles mixed with said storage liquid.

18. A method according to claim 17, comprising:

flow cytometry evaluation for virus particles of samples each comprising at least a portion of a different said filtrate, wherein the flow cytometry evaluation comprises hydrodynamically focusing a flow of each said sample and flowing each hydrodynamically focused sample through a flow cytometry investigation cell at a flow rate maintained in a range of from 500 to 3000 nanoliters per minute; and prior to the flow cytometry evaluation, marking the at least a portion of each said filtrate with at least one fluorescent marker;

wherein:
the flow cytometry evaluation comprises sequentially subjecting to flow different ones of the plurality of said samples; and the sequentially subjecting to flow cytometry comprises sequentially removing said samples from different filtrate collection containers of a filtrate collection plate of the sample filtration unit with an autosampler and sequentially delivering said samples from the autosampler to a flow cytometer.

19. A method according to claim 17, wherein the buffer solution reagent is a Tris-HCl buffer solution reagent and the buffer storage liquid is a Tris-HCl buffer storage liquid.

* * * * *